United States Patent [19]

Michaelson et al.

[11] 4,413,151

[45] Nov. 1, 1983

[54] PROCESS FOR HYDROXYLATING OLEFINS USING A SUPPORTED OSMIUM CATALYST

[75] Inventors: Robert C. Michaelson, Waldwick; Richard G. Austin; Donald A. White, both of Ridgewood, all of N.J.

[73] Assignee: Exxon Research & Engineering Co., Florham Park, N.J.

[21] Appl. No.: 397,997

[22] Filed: Jul. 14, 1982

[51] Int. Cl.$^3$ .................. C07C 29/03; C07C 31/20
[52] U.S. Cl. ............................. 568/860; 502/159; 502/164; 502/167; 502/170; 568/458; 568/811; 568/821; 568/833; 568/838; 568/847; 549/243; 560/186; 562/587; 502/174; 502/200; 502/226; 502/230

[58] Field of Search ............... 568/860, 839, 833, 821, 568/811, 847, 458; 549/243; 560/186; 562/587; 260/397.2

[56] References Cited

U.S. PATENT DOCUMENTS 2,813,130  11/1957  Keeler et al. ................ 568/860
4,314,088   2/1982  Austin et al. ................ 568/860

Primary Examiner—J. E. Evans
Attorney, Agent, or Firm—Robert A. Maggio

[57] ABSTRACT

A process for hydroxylating olefins using a supported osmium catalyst such as $Os_3(CO)_{12}$ adsorbed on a support, such as MgO, and optionally in conjunction with a co-catalyst such as NaI, is disclosed.

51 Claims, No Drawings

PROCESS FOR HYDROXYLATING OLEFINS USING A SUPPORTED OSMIUM CATALYST

BACKGROUND OF THE INVENTION

The present invention relates to processes for hydroxylating olefins, preferably in the liquid phase, in the presence of a supported osmium catalyst, and a cocatalyst.

Processes for the production of glycols such as ethylene glycol, from olefins are well known in the art.

For example, it is well known from the technical literature and patents that olefins can be effectively oxidized to their corresponding vicinal diols with a strong oxidizing agent in the presence of catalytic amounts of specific osmium containing compounds, particularly osmium tetroxide.

The patent literature directed to osmium containing hydroxylation catalysts describes various osmium oxides used in homogeneous reaction systems in conjunction with specific oxidants. The primary oxide catalyst employed in these patents is $OsO_4$, a highly volatile (B.P. 130° C.) and toxic substance. Ordinarily, the toxic nature of $OsO_4$ alone, while troublesome to some extent, could be dealt with by reasonably economic precautions. However, the combined properties of high volatility and toxicity (human tolerance is 0.002 mg/m$^3$ of air) render this compound extremely dangerous necessitating large capital expenditures in plant safety equipment and design if one attempts to commercialize a process employing this compound as a catalyst for use in homogeneous reaction systems. It is for this reason that commercialization of $OsO_4$ based plants has infrequently occurred in the past, if at all. If commercialization is attempted, the aforedescribed capital investment in safety equipment must reduce the profit margin on the products made by these processes.

Accordingly, it would be of extreme economic significance if alternative osmium catalysts could be identified which possess the property of low volatility and/or low toxicity (in relation to $OsO_4$), together with processes for using the same to achieve glycol product selectivity and yield comparable to or better than the conventional $OsO_4$ catalyst.

One important step in this direction is described in U.S. patent application Ser. No. 310,217, filed Oct. 9, 1981 of common assignee herein by R. Michaelson and R. Austin. This application discloses the use of various osmium halides and oxyhalides in the presence or absence of a wide variety of co-catalysts. However, these osmium containing catalysts are employed in a homogeneous reaction mixture. Consequently, these catalysts in commercial practice are circulated through the downstream processing steps which remove glycol products and any by-products. This leads to the use of costly equipment to recover the expensive osmium containing catalysts for recycle to the hydroxylation reactor. This disadvantage is inherent in all conventional processes for hydroxylating olefins using osmium containing catalysts since, to the best of applicants' knowledge, all of these processes employ unsupported homogeneous osmium catalysts to directly hydroxylate olefins thereby necessitating some type of catalyst recovery procedure.

The advantages of using a supported osmium catalyst in this area of catalysis are substantial, yet to date such use has not been disclosed in the prior art. For example, use of a supported catalyst permits the use of a fixed bed containing the supported osmium catalyst through which is passed the reaction mixture. Consequently, the osmium catalyst is contained in a localized area, thereby eliminating recovery and recycle equipment as well as the safety equipment needed to avoid contamination of the environment at the point where product is recovered. In addition, placing the osmium catalyst on a support would, in most instances, provide a means for facilitating the handling of the osmium catalyst and/or reduce its volatility, particularly where the osmium compound chemically reacts with the support.

Commonly assigned U.S. Pat. No. 4,314,088 and a continuation-in-part thereof, namely, U.S. patent application Ser. No. 310,099 filed Oct. 9, 1981 by R. Austin and R. Michaelson collectively, disclose the use of various halide containing co-catalysts in conjunction with osmium tetroxide catalyst and organohydroperoxide oxidants to hydroxylate olefins. The halide containing co-catalysts include alkali and alkaline earth metal halides hydrogenhalides, quaternary hydrocarbyl phosphonium halides, halogens, and transition metal halides. While it is disclosed generally in the aforenoted CIP application that the hydroxylation reaction can be conducted in a heterogeneous system, this application does not disclose a heterogeneous system containing a supported osmium catalyst.

U.S. patent application Ser. No. 310,097 filed Oct. 9, 1981 by R. Austin and R. Michaelson is directed to the hydroxylation of olefins using oxygen as an oxidant, a catalytically active metal oxide catalyst such as $OsO_4$, and at least one transition metal salt co-catalyst. This application also discloses generally that the hydroxylation reaction can be conducted in a heterogeneous system but makes no reference to a heterogeneous system containing a supported osmium catalyst.

U.S. patent application Ser. No. 399,270 filed July 19, 1982, by R. Austin and R. Michaelson is directed to a process for hydroxylating olefins in the presence of an organohydroperoxide oxidant, as osmium containing catalyst and an organic halogenated hydrocarbon co-catalyst. The disclosure relating to supported osmium catalysts in this application as a source of osmium is derived from the process of the present invention.

Commonly assigned U.S. patent application Ser. No. 394,414, filed July 1, 1982 by Michaelson and Austin, is directed to the use of carboxylate salts as co-catalysts for use in conjunction with osmium oxides as a catalyst and organohydroperoxide as oxidant to hydroxylate olefins.

Various supported osmium compounds, have been reported in the literature and been the subject of considerable research as illustrated and described in the following publications: "Studies of Ethane Hydrogenolysis Over Group VIII Metals: Supported Osmium and Iron" by Sinfelt and Yates, J. of Catalysis, Vol. 10, p. 362–367 (1968); "Cyclopropane-Hydrogen Reaction Over the Group VIII Novel Metals" by Betta, Cusumano, and Sinfelt, J. of Catalysis, Vol. 19, p. 343–349 (1970); "Electron Microscopy Studies of Metal Clusters: Ru, Os, Ru-Cu, and Os-Cu" by Prestridge, Via, and Sinfelt, J. of Catalysis, Vol. 50, p. 115–123 (1977); "Extended X-ray Adsorption Fine Structure (EXAFS) of Dispersed Metal Catalysts" by Via and Sinfelt, J. of Chem. Phys. Vol. 71(2), p. 690–691 (July 1979); and "Co Hydrogenation Catalyzed by Magnesia-Supported Osmium Derived from $Os_3(CO)_{12}$" by Deeba, Scott, Barth and Gates, J. of Catalysis, Vol. 71, p. 373–380 (1981). However, most existing supported osmium compounds have been employed under reducing conditions for hydrogenation catalysis and not for hydroxylation catalysis which occurs under oxidizing conditions.

U.S. Pat. No. 4,182,722 discloses a process for oxidizing acyclic and cyclic monoolefins with oxygen or oxygen containing gas using an ion-exchanged bimetallic solid catalyst to form epoxyalcohols. The bimetallic catalyst requires as exchanged ions at least one transition metal from Group V of the Periodic Table, such as vanadium, and at least one transition metal from Group IB or VIII, such as cobalt, copper, iron, rhodium, ruthenium, osmium, or iridium. Thus, the nature of the supported catalyst, the type of reaction which is catalyzed, and the oxidant employed all are different from that employed in the present invention.

None of the prior art which applicants' are aware disclose supported osmium catalysts for directly hydroxylating olefins to their corresponding diols. However, the following patents are discussed to provide a general background of the olefin hydroxylation prior art.

U.S. Pat. No. 2,414,385 discloses the use of hydrogen peroxide and a catalytically active oxide, such as osmium tetroxide, dissolved in an essentially anhydrous non-alkaline, inert, preferably organic, solvent, to convert, by oxidation, unsaturated organic compounds to useful oxygenated products such as glycols, phenols, aldehydes, ketones, quinones and organic acids. The formation of glycols is achieved by conducting the reaction at temperatures of between several degrees below 0° C. and 21° C. Such low reaction temperatures drastically, and disadvantageously, reduce the reaction rate to commercially unacceptable levels. At temperatures greater than 21° C., the formation of aldehydes, ketones and acids is favored.

U.S. Pat. No. 2,773,101 discloses a method for recovering an osmium containing catalyst such as osmium tetroxide, by converting it to the non-volatile osmium dioxide form, distilling the hydroxylation product, reoxidizing the osmium dioxide to the volatile osmium tetroxide, and then recovering the same by distillation. Suitable oxidizing agents used to oxidize olfins, and reoxidize the osmium dioxide, include inorganic peroxides such as hydrogen peroxide, sodium peroxide, barium peroxide; organic peroxides, such as t-butyl peroxide or hydroperoxide, benzoyl peroxide; as well as other oxidizing agents such as oxygen, perchlorates, nitric acid, chlorine water and the like. As with other methods of the prior art, the above process yields undesirable by-products (see col. 1, line 55) thus reducing the selectivity of the process.

British patent specification No. 1,028,940 is directed to a process for regenerating osmium tetroxide from reduced osmium tetroxide by treatment of the latter with moleculr oxygen in an aqueous alkaline solution. More specifically, it is disclosed that when osmium tetroxide is used by itself as an oxidizing agent, or as a catalyst in conjunction with other oxidizing agents, to oxidize hydrocarbons the osmium tetroxide becomes reduced, and in its reduced form is less active than osmium tetroxide itself. Consequently, by conducting the oxidation reaction in the presence of an alkaline medium and supplying oxygen to the medium throughout the process, the osmium tetroxide is maintained in a high state of activity. The oxidation products disclosed include not only ethylene glycol from ethylene but also organic acids from such compounds as vicinal glycols, olefins, ketones and alcohols.

U.S. Pat. No. 4,255,596 is directed to a process for preparing ethylene glycol in a homogeneous single-phase reaction medium using ethylbenzene hydroperoxide as the oxidizing agent dissolved in ethylbenzene and osmium tetroxide as the catalyst. The pH of the reaction medium is maintained at about 14 by the presence of tetraalkyl ammonium hydroxide. A small amount of water can dissolve beneficially in the medium to reduce by-product formation and improve selectivity to the glycol.

U.S. Pat. No. 4,049,724 describes the preparation of glycols from alkenes and from unsaturated alcohols in an aqueous system using osmium tetroxide and specifying stable and water-soluble aliphatic hydroperoxides, such as t-butyl hydroperoxide, while a critical pH of 8 to 12 is maintained by a suitable combination of alkali metal buffering compounds. The preparation of propylene glycol utilizing t-butyl hydroperoxide is exemplified in the patent at a selectivity based on the hydroperoxide of 45%.

Japanese Patent Application No. Sho 54-145604, published Nov. 14, 1979 is directed to a process for hydroxylating olefins in the presence of $OsO_4$, a quaternary ammonium salt such as tetraethyl ammonium bromide, and a peroxide including organoperoxides and $H_2O_2$ as the oxidant.

U.S. Pat. No. 3,335,174 is directed to the use of water hydrolyzable Group Vb, VI-b and VII metal halides and oxyhalides (e.g., $OsCl_3$) as hydroxylation and esterification catalysts in conjunction with aqueous $H_2O_2$ as an oxidant. However, the process for using this catalyst requires the presence of lower aliphatic hydrocarbon acids such as glacial, formic, acetic and propionic acid as solvents. Under these conditions the reaction times vary from $\frac{1}{2}$ to 4 hours, but at the shorter reaction times it is disclosed that substantial amounts of epoxide result. The only yield disclosed is obtained in connection with tungsten hexachloride in Example 1. This yield is extremely low, i.e., 22%, and includes both half-acetate and diol. Thus, among the major disadvantages of the process described in this patent are the low selectivities to diol and the corrosiveness of metal halides in the presence of glacial acids such as acetic acid.

See also: U.S. Pat. No. 3,317,592 (discloses production of acids and glycols using oxygen as oxidant, $OsO_4$ as catalyst at pH 8 to 10); U.S. Pat. No. 3,488,394 (discloses hydroxylation of olefins by reacting olefin and hypochlorite in the presence of $OsO_4$); U.S. Pat. No. 3,846,478 (discloses reaction of hypochlorite and olefin in an aqueous medium and in the presence of $OsO_4$ catalyst to hydroxylate the olefin); U.S. Pat. No. 3,928,473 (discloses hydroxylation of olefins to glycols with $O_2$ oxidant, octavalent osmium catalyst (e.g. $OsO_4$), and borates as promoter); U.S. Pat. No. 3,931,342 (discloses a process for recovering glycols from an aqueous solution containing alkali metal borate and osmium compounds (e.g. $OsO_4$); U.S. Pat. No. 3,953,305 (discloses use of $OsO_4$ catalyst for hydroxylating olefins which is regenerated by oxidizing hexavalent osmium with hexavalent chromium and electrochemically regenerating hexavalent chromium); U.S. Pat. No. 4,203,926 (discloses ethylbenzene hydroperoxide as oxidant used in two-phase system to hydroxylate olefins in presence of $OsO_4$ and cesium, rubidium and potassium hydroxides); U.S. Pat. No. 4,217,291 (discloses the oxidation of Osmium (III) or (IV) in an ionic complex with oxygen and an alkali metal, ammonium, or tetra (-lower) alkyl ammonium cation to a valency of greater than +5+organohydroperoxides); U.S. Pat. No. 4,229,601 (discloses the use of cesium, rubidium and potassium hydroxides as promoters for OsO4 catalyst and t-butyl hydroperoxide oxidant for hydroxylating olefins); and U.S. Pat. No. 4,280,924 (discloses a process for regenerating perosmate catalyst, e.g., cesium, rubidium and potassium perosmate).

Accordingly, there has been a continuing search for catalysts capable of improving processes for the hydroxylation of olefins. The present invention is a result of this search.

SUMMARY OF THE INVENTION

In one aspect of the present invention there is provided a process for hydroxylating olefins which comprises reacting in admixture at least one olefinic compound having at least one ethylenic unsaturation, with water, and at least one oxidant selected from the group consisting of organic hydroperoxide, $H_2O_2$, and oxygen in the presence of a catalyst composition under conditions and in a manner sufficient to convert at least one of said ethylenic unsaturation to its corresponding diol said catalyst composition comprising:

(a) at least one osmium compound adsorbed on at least one support to form a supported osmium catalyst, said osmium compound being capable of catalyzing said hydroxylation reaction when adsorbed on said support, said supported osmium catalyst being insoluble in said admixture under hydroxylation reaction conditions; and optionally (b) at least one co-catalyst capable of increasing at least one of the rate and selectivity of the hydroxylation reaction to product diol relative to the rate and selectivity in the absence of said co-catalyst.

DESCRIPTION OF PREFERRED EMBODIMENTS

In accordance with the present invention, at least one olefin containing at least one ethylenic unsaturation is reacted with at least one oxidant, and water in the presence of at least one supported osmium containing catalyst, and optionally but preferably at least one co-catalyst, under conditions and in a manner sufficient to hydroxylate at least one of said ethylenically unsaturated groups to its corresponding diol group.

Osmium Compound

In accordance with the present invention, it has been found that the oxidation state of osmium in the supported osmium catalyst as initially added to the reaction mixture is not critical to catalytic activity, particularly when an appropriate halide containing co-catalyst is employed as described hereinafter, i.e., any osmium compound, when adsorbed on a suitable support, and subjected to hydroxylation conditions as described herein, itself possesses, or is converted under such hydroxylation conditions to a species which possesses, the capability of catalyzing the hydroxylation of olefins.

The present invention is also believed to be the first instance wherein it has been shown that an osmium compound when adsorbed on a support, will not disassociate from the support under hydroxylation conditions as described herein.

The above described discoveries permit and motivate one to flexibly tailor the identity of the osmium compound and support on which it is deposited to achieve an extremely efficient heterogeneous supported catalyst system for hydroxylating olefins. In selecting the particular osmium compound for use in the present invention, the volatility and/or toxicity of the compound, its compatibility and degree of bonding or adherence to the support, and its activity in the system employed will be taken into consideration.

More specifically, included within the scope of osmium compound (the term "osmium compound" is defined herein broadly to also include osmium metal as well as ionic and neutral complexes of osmium and a ligand) which can be adsorbed on a support include osmium carbonyls, osmium metal, halogenated osmium compounds, osmium oxides, ionic osmium compounds, and osmium complexes.

Osmium carbonyls include $Os(CO)_5$, $Os_2(CO)_9$, $Os_3(CO)_{12}$, $Os_5(CO)_{16}$, $Os_6(CO)_{18}$, $Os_7(CO)_{21}$, and $Os_8(CO)_{23}$. The most preferred osmium compound of this class is $Os_3(CO)_{12}$. These compounds can be prepared by conventional methods as described in "Inorganic Synthesis", F. A. Cotton ed. Vol. 13, p. 92 (1972), and "Quarterly Reviews", Vol. 24, p. 498 (1970).

Representative halogenated osmium compounds are disclosed in U.S. patent application Ser. No. 310,217, filed Oct. 9, 1981 the disclosure of which is herein incorporated by reference.

For example, osmium-halogen containing compounds include osmium halides and osmium oxy halides, and complexes thereof, (all of the above being referred to herein collectively as osmium-halides) such as those represented by the structural formulae: $Os(X)_n$ (e.g., $OsX_3$, $OsX_4$, and $OsX_5$); $Os(OX)X_3$; $OsOX_4$; $OsO_3X_2$; $OsONX_4$; $(M)_{n'}[OsX_6]^{-2}$; $(M)_{n'}[OsO_2X_4]^{-2}$; $M^{+1}[Os(OH)X_5]^{-1}$; $(M)_{n'}[OsO_4X_2]^{-2}$; $(M)_{n'}[OsO_2(OH)X_2]^{-2}$; $(M)_{n'}[OsNX_5]^{-2}$; and mixtures thereof: wherein X is halogen independently selected from the group consisting of F, Cl, Br and I; n is an integer which can vary from 1 to 6 (e.g. 3 to 5), M is a cation including cations of alkali metals, (e.g., Li, Na, K, Rb, Cs, Fr), alkaline earth metals (e.g., Be, Mg, Ca, Sr, Ba, Ra), ammonium (i.e., NH4+), tetrahydrocarbyl ammonium (e.g. (R)4N+) and tetrahydrocarbyl phosphonium (e.g. (R)4P+) said tetrahydrocarbyl groups being as defined in connection with Group 5 co-catalysts discussed below; and n' is a number which is selected in conjunction with the valence of cation M to achieve a neutral complex; preferably $n'$ is 1.

Representative examples of such compounds include $OsF_3$, $OsCl_3$, $OsBr_3$, $OsI_3$, $OsF_4$, $OsCl_4$, $OsBr_4$, $OsI_4$, $OsF_5$, $Os(OH)Cl_3$, $Os(OH)F_3$, $OsOF_4$, $OsOCl_4$, $OsO_3F_2$, $OsONCl_4$, $K_2[OsCl_2Br_2I_2]$, $(NH_4)_2[OsF_6]$, $Ca[OsI_6]$, $Li_2[OsO_2Cl_4]$, $(CH_3CH_2)_4N[Os(OH)Cl_5]$, $Mg[OsO_4F_2]$, $Na_2[Os(OH)_2Cl_2]$, $Ba[OsCl_5N]$, $K_2[OsNCl_5]$, $(CH_3CH_2)_4P[Os(OH)Br_5]$, $Mg[OsNBr_5]$, $Na_2[Os(OH)_2Cl_2]$, $Ba[OsCl_5N]$, $K_2[OsNCl_5]$, $K_2[OsNBr_5]$, and mixtures thereof.

The preferred compounds of this class are those having a boiling point at atmospheric pressure of typically greater than about 130° C., preferably greater than about 150° C., and most preferably greater than about 175° C.

The most preferred compounds are those represented by the structural formula $OsX_3$ such as $OsCl_3$.

The compounds having the formula $Os(X)_n$ can be prepared by the general methods described in "Advanced Inorganic Chemistry" by Cotton and Wilkinson (hereinafter Cotton and Wilkinson), p. 909 (4th ed. 1980).

Compounds having the formula $OsOX_4$ and $OsO_3X_2$ can be prepared by the method described in the "J.

Inorganic Nuclear Chemistry" by Hepworth and Robinson, Vol. 4, p. 24 (1957).

Compounds having the formula Os(OH)X$_3$ can be prepared by the method described in "Comprehensive Inorganic Chemistry", Trotman-Dickenson (ed.) vol. 3, p. 1217 (1973).

Compounds having the formula OsONX$_4$ can be prepared by the method described in "Comprehensive Inorganic Chemistry" described above at vol. 3, p. 1233.

Compounds having the formula $(M)_{n'}[OsX_6]^{-2}$ can be prepared by the general method described in Cotton and Wilkinson, p. 919.

Compounds having the formula $(M)_{n'}[OsO_2X_4]^{-2}$ can be prepared by the general method described in Cotton and Wilkinson, p. 917.

Compounds having the formula $M^{+1}[Os(OH)X_5]^{-1}$ can be prepared by the general method described in "Z. Anorg. Allgen. Chem" by Krauss and Wilken (hereinafter Krauss and Wilken) vol. 137, p. 349 (1924).

Compounds having the formula $(M)_{n'}[OsO_4X_2]^{-2}$ can be prepared by the method described in Krauss and Wilken, vol. 145, p. 151 (1925).

Compounds having the formula $(M)_{n'}[OsO_2(OH)X_2]^{-2}$ can be prepared by the method described in Cotton and Wilkinson, p. 914.

Compounds having the formula $(M)_{n'}[OsNX_5]^{-2}$ can be prepared by the method described in "Inorganic Synthesis", by E. G. Rochow, vol. 6, p. 204 (1960).

The disclosures of all of the above references illustrating the methods of preparation of the aforenoted osmium-halide compounds are herein incorporated by reference.

Representative osmium oxides include OsO$_2$, OsO$_3$, OsO$_4$, and mixtures thereof.

Representative ionic osmium oxide compounds are described in U.S. Pat. No. 4,217,291 the disclosure of which is herein incorporated by reference. These ionic osmium compounds can be represented by the formula:

$$M'_xOsO_y \quad (I)$$

wherein M' is a cation of an alkali or alkaline earth metal, ammonium, or tetraalkyl ammonium, preferably tetraalkyl ammonium in which the alkyl group has from about 1 to about 5 carbons, and x and y are numbers such that 2y-x is the valence of the osmium in any compound defined by this formula. While the preferred ionic osmium compounds of this class are the perosmates (M'$_2$OsO$_5$) other ionic osmium compounds such as M'$_2$OsO$_4$ (known as osmates), M'$_2$OsO$_3$, and M'OsO$_2$ can also be employed.

Representative of osmium complexes include those which form with ligands of CO, PR'$_3$, amines, nitride, $\pi$-bonded cyclopentadienyl ($\pi$-CPD), and mixtures thereof.

Illustrative carbonyl containing osmium complexes can be represented by the structural formulae [Os(CO)X$_5$]$^{-2}$; [Os(CO)$_2$X$_4$]$^{-2}$; [Os(CO)$_4$X$_2$]$^{-2}$; and [Os(CO)$_3$X$_3$]$^{-1}$ wherein X is halogen as described above in connection with osmium oxy halides. Preferably X is chlorine, bromine or iodine.

Representative examples of suitable osmium carbonyl complexes include [Os(CO)Cl$_5$]$^{-2}$, [Os(CO)I$_5$]$^{-2}$, [Os(CO)$_2$Br$_4$]$^{-2}$, [Os(CO)$_2$Cl$_4$]$^{-2}$, [Os(CO)$_3$I$_3$]$^{-1}$, [Os(CO)$_3$Cl$_3$]$^{-1}$, [Os(CO)$_4$I]$^{-2}$, and [Os(CO)$_4$Cl]$^{-2}$.

Illustrative osmium phosphine complexes can be represented by the structural formula:

$$Os(X'')_a(Y)_b(PR'_3)_c \quad (II)$$

wherein X'' is independently selected from hydrogen, (e.g., hydrido) cyclopentadienyl (CPD), and halogen (preferably iodine); Y is independently selected from NO, CO, NH$_3$, and N$_2$; R' is hydrocarbyl group independently selected from alkyl, typically alkyl of from about 1 to about 10, preferably from about 1 to 5, most preferably from about 1 to 3 carbons, aryl, typically aryl of from about 6 to about 14, preferably from about 6 to about 10, most preferably about 6 carbons, alkaryl and aralkyl wherein the alkyl and aryl groups thereof are as defined immediately above, "a" and "b" are numbers of from 0 to about 3, "c" is a number of 2 to 4 (e.g. 2 to 3) and the sum of a, b, and c is selected in conjunction with the valence of Os to achieve a neutral complex.

Representative examples of suitable osmium phosphine complexes include OsH$_2$(N$_2$)(P$\phi_3$)$_3$; OsH$_2$(P$\phi_3$)$_4$; OsCl$_2$(CO)(P$\phi_3$)$_2$; Os(CO)$_3$(P$\phi_3$)$_2$; OsHCl(CO)(P$\phi_3$)$_3$; OsCl(CO)(NO)(P$\phi_3$)$_2$; OsCl$_2$(PO$_3$)$_3$; OsCl$_3$(NO)(P$\phi_3$)$_2$; OsCl(NO)(P$\phi_3$)$_2$; OsHCl(CO)(PEt$_2\phi$)$_3$; OsCl$_2$(NH$_3$)(PEt$_2\phi$)$_3$; Os($\pi$-CPD)$_2$(CO)(P$\phi$)$_2$, and mixtures thereof; "Et" representing ethyl, "$\phi$" representing phenyl, and $\pi$-CPD representing pi-bonded cyclopentadienyl.

Illustrative osmium amine complexes include aromatic amine complexes illustrated by [Os(bipy)$_3$]$^{+2}$ wherein bipy is 2,2'-bipyridine, and [Os(NH$_3$)$_5$X]$^{+2}$ wherein X is halogen, preferably I.

Illustrative osmium nitride complexes include [OsO$_3$N]$^-$; K[OsO$_3$N]; and OsO$_3$NC(CH$_3$)$_3$.

Illustrative $\pi$-CPD complexes include Os($\pi$-CPD)$_2$.

Methods for preparing the aforedescribed osmium complexes are conventional and are summarized in Cotton and Wilkinson "Advanced Inorganic Chemistry" pages 1000–1017 (3rd ed. 1972).

II. Support

The material on which the osmium compound is supported can be inorganic or organic but must be insoluble in the reaction mixture under reaction conditions and be capable of physically and/or chemically adsorbing the osmium compound to the extent that it retains a catalytically effective amount of the osmium compound adsorbed thereon.

The catalyst support provides not only the required surface for the osmium compound, but gives physical strength and stability to the same.

The surface area of the support is not critical and typically can vary from about 0.5 to about 400, preferably from about 1 to about 200, and most preferably from about 30 to about 100 m$^2$/g. A desired form of inorganic support is one which has a rough enough surface to aid in retaining the catalyst adhered thereto during handling and under reaction conditions. The support may vary in size but typically is from about 3 to about 400, preferably from about 5 to about 200, most preferably from about 6 to about 100 mesh in the Tyler Standard screen size. Support particles as large as 1 inch in diameter are satisfactory.

Supports much smaller than 325 to 400 mesh normally cause an undesirable pressure drop in the reactor.

The support material is not necessarily inert, that is, the particular support may cause an increase in the catalyst efficiency by its chemical or physical nature or both, but should not adversely influence the hydroxylation reaction. Moreover, the support may impart catalytic activity to an otherwise catalytically inactive, or substantially inactive, material in the absence of the support such as in the instance of osmium metal.

The amount of osmium compound adsorbed on the support is any amount effective to increase the rate and/or selectivity of the hydroxylation reaction relative to the absence of the osmium compound. Thus, while any effective amount may be adsorbed on the support, such effective amounts typically will be from about 0.01 to about 75, preferably from about 0.05 to about 20, most preferably from about 0.1 to about 10.0%, by weight, based on the combined weight of osmium compound and support.

The amount of supported osmium catalyst employed during hydroxylation will likewise be any amount effective to increase the rate and/or selectivity of the hydroxylation reaction relative to the absence of the supported catalyst. The most convenient way to express the amount of supported osmium catalyst (i.e., osmium compound+support) having the aforedescribed amounts of osmium compound adsorbed thereon is as a ratio of the weight of the supported osmium catalyst in contact with the weight of reaction mixture at any given time during the reaction.

Accordingly, while any effective amount of supported osmium catalyst may be employed, it is contemplated that such effective amounts constitute a ratio of parts by weight of supported catalyst to parts by weight of reaction mixture in contact therewith of typically from about 1:0.8 to about 1:20, preferably from about 1:1 to about 1:10, and most preferably from about 1:1 to about 1:4.

Representative supports include alkaline earth metal oxides including MgO, CaO, BaO, BeO and SrO; $Sc_2O_3$; $Y_2O_3$; oxides of the Lanthanide series of elements represented by the formula $Ln_2O_3$, wherein Ln represents a lanthanide element (i.e., atomic number 58 to 71); alumina ($Al_2O_3$); silica ($SiO_2$); silica gel; silica-alumina; silicon carbide; titania ($TiO_2$); titania-silica; carbon; activated carbon; $Al_2O_3.B_2O_3$, $SiO_2.B_2O_3$, and mixtures thereof; alkaline earth metal orthosilicates such as $Ca_2SiO_4$, $Mg_2SiO_4$; heteropolyanions such as heteropoly tungstates, heteropoly molybdates (e.g., $Na_3PMo_{12}O_{40}$) and the like; and insoluble halogen salts such as $Hg_2I_2$, $HgI_2$, and $PbI_2$.

Another class of suitable supports include ionic materials onto which the osmium compound can be adsorbed. Included within the scope of ionic supports are zeolites, and ionic polymeric compounds.

Suitable zeolites which can function as supports in accordance with the present invention are exemplified by crystalline aluminosilicate zeolites, preferably zeolites of the faujasite structure. Typically, such faujasite materials possess a $SiO_2:Al_2O_3$ mole ratio in the range of about 2 to about 8 and characteristically have pore diameters in excess of 6 angstroms, which is appropriate for admission of reactants, and to allow exit of the hydroxylated product. The X- and Y-type zeolites are suitable for use as supports herein, with the X-type being preferred. Type X zeolite has a typical oxide formula: $Na_2O.Al_2O_3.2.5SiO_2.6H_2O$ although the mole ratio of $SiO_2:Al_2O_3$ can typically vary from about 2:1 to about 3:1. Type Y zeolite has a typical oxide formula: $Na_2O.Al_2O_3.4.8SiO_2.8.9H_2O$ although the mole ratio of $SiO_2Al_2O_3$ can typically vary from about 3:1 to about 6:1. Type L zeolites, natural faujasite materials and mordenites are examples of other zeolites having appropriate pore size and structure for use as a support herein.

In general, zeolites having suitable properties can be utilized, whether obtainable as natural materials or prepared synthetically, and can be obtained from commercial sources or prepared by appropriate laboratory crystallization procedures.

The ionic and porous nature of zeolites permits incorporation of the osmium compound therein by conventional ion exchange and/or impregnation procedures as described hereinafter. Similar considerations also apply with respect to ionic polymer supports.

Polymeric ionic support materials typically are employed in porous solid form such as beads, powders, granules, and the like. Suitable polymeric supports are stable to hydroxylation reaction conditions, and sufficiently adsorptive toward the reaction mixture to achieve good contact therewith with the osmium catalytic sites present therein. Accordingly, the polymer must be sufficiently inert and rugged when in contact with the hydroxylation reaction mixture to be resistant to the reaction mixture and easily separated therefrom; and not be abraded, dissolved, decomposed or converted into a soft pulpy gel difficult to separate from the reaction mixture.

Representative classes of suitable ionic polymer supports include conventional weak and preferably strong, acid (cation) or base (anion) exchange resins. Ion exchange resins typically comprise as a back-bone polymer, a polymer crosslinked with a difunctional monomer, to which is attached functional acid or base groups exchanged with various cations or anions (i.e., counter ions) respectively. Representative of weak-acid cation exchange resins include those based on polymers of acrylic or methacrylic acid esters crosslinked with divinyl benzene (DVB). The ester groups are hydrolyzed to produce the functional acid group.

Representative of strong acid cation exchange resins include sulfonated co-polymers of styrene and DVB. Sulfuric acid, sulfurtrioxide, and chlorosulfonic acids can be used for such sulfonation.

Representative of strong-base anion exchange resins include those based on a styrene-DVB co-polymer having an amine functional group, pendant from the aromatic portion of the co-polymer. The base strength of the resin can be varied by varying the nature of the amine functional group from primary to tertiary. The counter ion, prior to incorporation of the osmium compound, for the acid exchange resin is preferably sodium, and for the base-exchange resin, hydroxyl, although any of the conventional counter ions associated with commercially available ion exchange resins can be employed. Other acid or base functional groups can be incorporated into the pendant aromatic groups of the resin tailored specifically to react, complex with, or facilitate adsorption of, the osmium containing compound.

Furthermore, the functional groups of the base ion exchange resin can be partially or completely exhausted (i.e. exchanged) with halide ions which can perform the function of the halide co-catalysts described herein. In this way, the base ion exchange resin support, supports not only the osmium compound but also the co-catalyst halide species resulting in an insolubilized catalytic and co-catalytic system.

Representative commercial ion-exchange resins include those sold under the following tradenames: DOWEX TM available from Dow Chem. Co.; DUOLITE TM available from Diamond Shamrock; AMBER- LITE available from Rohm and Haas Co.; and NAL-CITE ™ available from Nalco Chemical Co.

The osmium compound is adsorbed on the support by any way capable of achieving physical and/or chemical adsorption of the latter by the support. Thus, adsorption methods are used which result in retention of the osmium compound in or on the support, and various materials and procedures have been found suitable for this purpose.

For example, an inorganic non-ionic support, e.g., MgO, can be suspended in a suitable solvent together with the osmium compound, preferably a saturated or supersaturated solution of the osmium compound, at room temperature and stirred for a period of from about 0.1 to about 72, preferably from about 0.5 to about 48, most preferably from about 0.5 to about 24 hours. The supension is then filtered and the recovered solids rinsed, with a suitable solvent. If the support and osmium compound are both dissolved, the solvent can be evaporated and the solids recovered after adsorption of the osmium compound by the support.

The suspension and/or solution of the support and osmium compound can be heated to elevated temperatures although this is not essential.

Suitable solvents and/or suspending media for the aforedescribed purposes include water, alcohols, ketones, ethers, aliphatic hydrocarbons, aromatic hydrocarbons, halogenated hydrocarbons, carboxylic acids and their derivatives such as amides.

Other adsorption methods include vapor phase deposition, electrodeposition, and sublimation.

When employing ionic supports, which typically possess pores capable of retaining the osmium compound, the adsorption method employed can utilize an ion-exchange procedure which results in valence-bonding of the osmium compound with the support and/or impregnation techniques.

For example, when employing zeolites or acid cation exchange resins, conventional ion exchange procedures can be employed to replace the support counter ion with a cationic osmium compound. Such ion exchange can be effected, for example, with solutions of cationic osmium species as described hereinabove, including osmium salts, such as osmium halides, nitrates, or sulfates. The weight ratio of osmium to support will vary depending on the number of anionic sites available on the support. However, it is preferable to maximize this ratio so that as many as possible anionic sites bond with the ionic osmium compound.

Similar exchange procedures can be employed with base anion exchange resins, with the exception that an anionic osmium compound species as described hereinabove is employed to effect the exchange.

Adsorption methods can also be employed which result in impregnation of the porous ionic support with the osmium compound. Thus, the osmium compound can conveniently be impregnated into the support by utilizing a solution of such osmium compound as a slurrying medium for support particles or as an impregnating medium to be adsorbed into the support. The media for incorporating the osmium compound do not necessarily have to completely dissolve the same and in fact may often contain suspended solids.

The supported osmium catalyst is adaptable for use in the various physical forms which are commonly used in a contact bed, or as a coating material on monolithic structures generally being used in a form to provide high surface area. The supported catalyst, can if desired, be composited with various binders which do not adversely affect the catalyst or the reactions in which the catalyst is to be employed.

Depending on the choice of osmium compound and support, the adsorption will be chemical and/or physical.

For example, osmium carbonyls are believed to react with alkaline earth supports such as MgO to form oxygen bonded clusters. Osmium halides or oxy halides are believed to react with metal oxide supports to form oxygen bonded compounds. Osmium oxides are believed to react with metal oxide supports to form osmium oxyanions. Valence bonding of ionic osmium compounds with ion-exchange resins has already been discussed.

The aforedescribed supported osmium catalysts are typically employed in conjunction with one or more promoters (also referred to herein as co-catalysts) which increase the rate and/or selectivity of the hydroxylation reaction. Such promoters or co-catalysts can be those conventionally employed in conjunction with $OsO_4$ as well as those disclosed in other commonly assigned U.S. patent applications.

For example, suitable promoters or co-catalysts include alkali (e.g., Li, Na, K, Rb, Cs, and Fr), and alkaline earth metal (e.g., Be, Mg, Ca, Sr, Ba and Ra): halides, oxides and/or hydroxides, carboxylates, arylo-ates, aryolates and pseudo halides; tetra hydrocarbyl ammonium: hydroxides, halides, carboxylates, arylo-ates, and aryolates; tetra hydrocarbyl phosphonium: hydroxides, halides, carboxylates, aryloates, aryolates; transition metal: halides, porphyrins, carboxylates, and aryloates; hydrogen halides; halogenated hydrocarbons such as alkyl, aryl, aralkyl, alkaryl and cycloalkyl halides; Group III-b (i.e., B, AL, Ga, In, Tl), IV-b (i.e., Si, Ge, Sn, Pb), V-b (i.e., N, P, As, Sb, Bi) and VI-b (i.e., S, Se, Te, Po) halides; and the halogens $F_2$, $Cl_2$, $I_2$, $Br_2$.

More specifically, suitable alkali and alkaline earth metal halide co-catalysts (referred to herein as Group I co-catalysts) include the Li, Na, K, Rb, and Cs iodides, bromides, chlorides and fluorides; and Mg, Ca, Sr, and Ba, iodides, bromides, chlorides, and fluorides and mixtures thereof. Preferred Group 1 co-catalysts include the Na, K, Rb, Cs, Mg and Ca halides.

Suitable alkali and alkaline earth metal hydroxide or oxide co-catalysts (referred to herein as Group 2 co-catalysts) include LiOH, NaOH, KOH, RbOH, CsOH, $Ca(OH)_2$, $Ba(OH)_2$, $Mg(OH)_2$, the corresponding oxides thereof, and mixtures thereof.

Preferred Group 2 co-catalysts include the Na, K, Rb, Mg and Ca hydroxides.

Suitable alkali and alkaline earth metal: carboxylate, aryloate, and aryolate co-catalysts (referred to herein as Group 3 co-catalysts) include those which possess as anions respectively:

(a) carboxylate anions represented by the structural formula:

(III)

wherein $R_1$ can be substituted or unsubstituted: alkyl, typically alkyl of from about 1 to about 10 carbons, preferably about 1 to about 5 carbons, and most preferably about 1 to about 3 carbons, cycloalkyl, typically cycloalkyl of from about 4 to about 20, preferably from about 5 to about 15, and most preferably from about 6 to about 10 carbons, or aralkyl, typically aralkyl wherein the aryl group thereof is as defined in connection with Ar of structural formula (IV) below and the alkyl group thereof is as defined immediately above; said $R_1$ substituents including: hydroxy; halide (i.e., F, Cl, Br, and I); ether groups represented by the structural formulae $-O-R_2$ and $-R_3-O-R_2$ wherein $R_2$ and $R_3$ are independently selected from the group consisting of alkyl, typically about $C_1$ to about $C_{10}$ alkyl, preferably about $C_1$ to about $C_5$ alkyl, and most preferably about $C_1$ to about $C_3$ alkyl; and ester groups represented by the structural formulae:

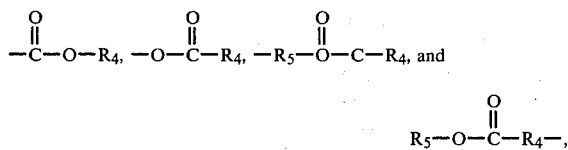

wherein $R_4$ and $R_5$ which may be the same or different are as defined in connection with $R_2$ and $R_3$; and mixtures thereof;

(b) aryloate anions represented by the structural formula:

(IV)

wherein Ar is selected from the group consisting of substituted and unsubstituted: aryl, typically aryl of from about 6 to about 14 carbons, preferably from about 6 to about 10 carbons, (e.g., 6 carbons), and alkaryl, typically alkaryl wherein the alkyl group is from about 1 to about 6 carbons, preferably from about 1 to about 3 carbons, and the aryl group thereof is as defined above, and wherein said substituents on the Ar group are as defined above in connection with $R_1$; and (c) aryolate anions represented by the structural formula:

(V)

wherein Ar is as described above in connection with structural formula (IV), and preferably is aryl.

Illustrative examples of such Group 3 co-catalysts include: sodium acetate, potassium acetate, calcium acetate, cesium acetate, magnesium acetate, potassium ethanoate, sodium propanoate, magnesium butanoate, strontium pentanoate, sodium benzoate, potassium benzoate, magnesium benzoate, calcium benzoate, sodium naphthoate, potassium naphthoate, beryllium naphthoate, sodium 4-(6-methyl-2-naphthyl)pentanoate, potassium 3-(7-methyl-1-naphthyl)propanoate, magnesium 2-(4-propyl-1-benzyl)ethanoate, calcium phenolate, sodium naphtholate, potassium naphtholate, sodium 3-(ethoxy)propanoate, potassium 4-(propoxy carbonyl)-butanoate, calcium 3-(propyl carbonyl oxy)propanoate, magnesium 2-(methyl carbonyl oxy methyl)acetate, beryllium 4-(ethoxy carbonyl methyl)butanoate, cesium 4-(ethoxy methyl)benzoate, sodium 3-(propoxy)naphthoate, potassium 4-(ethoxy carbonyl)benzoate, barium 2-(hydroxy)acetate, rubidium 2-chloropropanoate, magnesium 4-bromobenzoate, magnesium phenolate, and mixtures thereof.

Preferred Group 3 co-catalysts include the Na, K, Rb and Cs acetates.

Suitable alkali and alkaline earth metal pseudo halide co-catalysts (referred to herein as Group 4 cocatalysts) include those which possess pseudo halide anions selected from the group consisting of: $SCN^-$, $SeCN^-$, $TeCN^-$, $OCN^-$, and $CNO^-$, and mixtures thereof.

Illustrative examples of such Group 4 co-catalysts include NaSCN, NaSeCN, KSeCN, CsSeCN, NaTeCN, KTeCN, NaOCN, NaCNO, KOCN, KCNO, CsOCN, CsCNO, CsTeCN, $Mg(SeCN)_2$, $Ca(TeCN)_2$, $Ca(OCN)_2$, $Ca(CNO)_2$ and mixtures thereof.

Preferred Group 4 co-catalysts include the Na, K, Rb and Cs thiocyanates.

Tetra hydrocarbyl ammonium or phosphonium salt co-catalysts (referred to herein as Group 5 co-catalysts) possess a cation and an anion. The respective cations can be represented by the respective structural formula $(R)_4N^+$ and $(R)_4P^+$ wherein R is a hydrocarbyl group independently selected from the group consisting of substituted and unsubstituted: alkyl, typically alkyl having from about 1 to about 30 carbons, preferably from about 1 to about 20 carbons, and most preferably from about 1 to about 10 (e.g. 1–5) carbons, aryl, preferably aryl having from 6 to about 14 carbons, and most preferably from 6 to about 10 carbons, and alkaryl and aralkyl wherein the aryl and alkyl groups thereof are as described immediately above; said R substituents being as defined in connection with the substituents of $R_1$ described above. Accordingly, the term hydrocarbyl is intended to include both substituted and unsubstituted groups, and mixtures thereof. The anion of the Group 5 co-catalysts are selected from the group consisting of hydroxy, halide, pseudo halide, carboxylate, aryloate and aryolate, said pseudo halide, said carboxylate, aryloate, and aryolate anions, being as defined above in connection with the anions of the alkali and alkali metal salt co-catalysts described above.

Illustrative examples of such Group 5 co-catalysts include tetra methyl ammonium bromide, tetra ethyl phosphonium chloride, tetra decyl phosphonium bromide, tetra phenyl ammonium chloride, tetra phenyl phosphonium bromide, dimethyl diethyl ammonium iodide, methyl triethyl phosphonium chloride, tetra butyl ammonium chloride, phenyl trimethyl ammonium bromide, phenyl trimethyl phosphonium chloride, phenyl triethyl ammonium iodide, phenyl triethyl phosphonium chloride, tetra ethyl ammonium hydroxide, tetra butyl ammonium hydroxide, tetra ethyl phosphonium hydroxide, phenyl triethyl ammonium hydroxide, phenyl trimethyl phosphonium hydroxide, tetra ethyl ammonium acetate, tetra butyl phosphonium acetate, phenyl triethyl ammonium acetate, phenyl trimethyl phosphonium acetate, tetra ethyl ammonium benzoate, phenyl trimethyl phosphonium benzoate, phenyl triethyl ammonium naphthoate, tetra ethyl ammonium phenolate, tetra butyl phosphonium naphtholate, tetra 2-(methoxy)ethyl phosphonium chloride, tetra 4-(propoxy methyl)phenyl ammonium bromide, di 3-(methoxy carbonyl)propyl -diethyl phosphonium iodide, di 4-(ethyl carbonyloxy)butyl-dimethyl ammonium chloride, tetra 5-(ethoxy carbonyl methyl)pentyl phosphonium bromide, tetra 4-hydroxy butyl ammonium acetate, tetra 3-chloropropyl phosphonium acetate, tetra methyl ammonium thiocyanate, tetra ethyl phosphonium selenio cyanate, tetra(4-methyl phenyl)ammonium chloride, tetra(3-phenyl-1-propyl)phosphonium bromide.

Preferred Group 5 co-catalysts include the unsubstituted tetra lower alkyl (e.g., $C_1$ to $C_5$ alkyl)ammonium hydroxides, iodides, bromides, fluorides, chlorides and acetates.

Transition metal containing co-catalysts (referred to herein as Group 6 co-catalysts) include those having a cation and anion wherein the transition metal cation is selected from the group consisting of cations of Fe, Co, Ni, Cu, V, Cr, Mn, Sc, Ti, Mo, Ru, Rh, Pd, and W, preferably Cu, Fe, Ni, Co and Mn, most preferably Cu, and mixtures thereof.

Anions of the Group 6 co-catalysts include halide, porphyrin (as defined in the Condensed Chemical Dictionary 9th ed. revised by G. Hawley (1977) including benzoporphyrins), pseudo halide, carboxylate and aryloate; said pseudo halide, carboxylate and aryloate anions being as defined generally in connection with the alkali and alkaline earth metal containing co-catalysts and as illustrated by specific examples of suitable anions in conjunction with other co-catalysts described herein.

Representative examples of Group 6 co-catalysts include $FeF_3$, $FeCl_3$, $FeBr_3$, $FeF_2$, $FeCl_2$, $FeBr_2$, $FeI_2$, $CoCl_2$, $CoF_3$, $CoF_2$, $NiF_2$, $NiBr_2$, $NiI_2$, $NiCl_2$, $CuF_2$, $CuBr_2$, $CuI_2$, $CuF_2$, $CuI$, $CuCl$, $CuBr$, $VF_5$, $VF_4$, $VF_3$, $VF_2$, $VCl_4$, $VCl_3$, $VBr_4$, $VBr_3$, $VI_3$, $CrF_2$, $CrF_3$, $CrF_4$, $CrF_5$, $CrF_6$, $CrCl_3$, $CrCl_4$, $CrBr_3$, $CrBr_4$, $CrI_3$, $MnCl_2$, $MnCl_3$, $MnCl_4$, $MnBr_3$, $MnI_3$, $ScCl_3$, $ScBr_3$, $ScF_3$, $TiCl_4$, $TiBr_4$, $TiF_4$, $MoCl_3$, $Mo_2Cl_{10}$, $MoBr_4$, $Mo_2F_9$, $MoF_6$, $MoF_5$, $RuF_5$, $RuF_3$, $RuF_4$, $RuF_6$, $RuCl_3$, $RuCl_4$, $RuCl_6$, $RuBr_6$, $RhF_3$, $RhF_4$, $RhF_6$, $PdF_2$, $PdCl_2$, $PdBr_2$, $PdI_2$, $WCl_6$, $WBr_5$, $WCl_3$, $WBr_3$, $WI_3$, copper acetate, copper naphthoate, copper benzoate, copper propanoate, iron acetate, iron benzoate, iron naphthoate, copper 4-ethyl benzoate, iron 4-butyl benzoate, nickel acetate, nickel benzoate, nickel naphthoate, copper decanoate, iron hexanoate, iron phthalocyanine, manganese phthalocyanine, copper phthalocyanine, nickel phthalocyanine, and the Fe, Mn, Cu, and Ni porphyrin salts.

Preferred Group 6 co-catalysts include copper bromide, chloride, iodide, and acetate; iron bromide, chloride, iodide and acetate; manganese bromide, chloride, and acetate, and mixtures thereof.

Suitable hydrogen halides (referred to herein as Group 7 co-catalysts) include HF, HCL, HBr and HI.

Preferred Group 7 co-catalysts include HI, HBr, and HCl.

Suitable halogenated hydrocarbons (referred to herein as Group 8 co-catalysts) are described in commonly assigned U.S. patent application Ser. No. 399,270, filed July 19, 1982, by R. Austin and R. Michaelson, the disclosure of which is herein incorporated by reference including any halogenated hydrocarbon compound, wherein the hydrocarbyl portion is selected from saturated aliphatic, saturated alicyclic, and aromatic.

More specifically, suitable Group 8 co-catalysts can be represented by the structural formula:

   (VI)

wherein R' can be inertly substituted or unsubstituted: alkyl, typically alkyl of from about 1 to about 20, preferably from about 1 to about 10, most preferably from about 1 to about 5 carbons, aryl, typically aryl of from about 6 to about 14, preferably 6 to about 10, most preferably 6 carbons, aralkyl and alkaryl wherein the alkyl and aryl groups thereof are as defined immediately above, cycloalkyl, typically cycloalkyl of from about 4 to about 20, preferably from about 5 to about 15, and most preferably from about 5 to about 10 carbon atoms; X is at least one halogen independently selected from the group consisting of F, Cl, Br and I, and preferably I and Br; n" is a number of from about 1 to about 10, preferably from about 1 to about 8 (e.g., 2 to 6), and most preferably from about 1 to about 6 (e.g., 2 to 4); and said R' substituents including hydroxy, ether and ester groups, said ether and ester substituents being as described in connection with $R_1$ of structural formula III. The term "inertly substituted" is defined herein to mean any organic or inorganic substituent which is stable under reaction conditions and does not adversely affect the performance of said co-catalyst, relative to the unsubstituted halogenated organic compound.

Representative examples of suitable Group 8 co-catalysts include iodomethane, bromomethane, 1-iodoethane, 1-bromoethane, 1,2-dibromoethane, 1-chloroethane, 1,2-dichloroethane, 1-iodopropane, 1-bromopropane, 1-chloropropane, 2-iodo-1-methylethane, 2-bromo-1-methylethane, 2-chloro-1-methylethane, 1-iodobutane, 2-iodobutane, 2-bromobutane, 1-chlorobutane, 2-methyl-2-iodopropane, 2-methyl-2-bromopropane, 1-iodo-1-methylpropane, 1-bromo-1-methylpropane, 1-chloro-1-methylpropane, 1-iodo-1,1-dimethylethane, 1-chloro-1,1-dimethylethane, 1-chloro-1,1-dimethylethane, benzyl iodide, phenyliodomethane, phenylchloromethane, phenylbromomethane, 1,2-dichlorobenzene, 2-bromoethanol, 2-chloroethanol, 2-iodoethanol, 1-phenyl-2-iodoethane, 1-phenyl-4,4-dichlorobutane, 1-(1,2-dichloroethyl) benene, 1-(1-chloropropyl)naphthylene and mixtures thereof.

Preferred Group 8 co-catalysts include iodomethane, bromoethane, 1-bromobutane, 1-iodobutane, 1-bromo-1,1-dimethylethane, 1-iodo-1,1-dimethylethane, 2-iodobutane, 2-bromobutane, 2-methyl-2-iodopropane, 2-methyl-2-bromopropane, 2-bromoethanol, 2-chloroethanol, 2-iodoethanol, and mixtures thereof.

The most preferred Group 8 co-catalyst contains iodine and includes 1-iodobutane, iodomethane, 2-iodobutane, 2-methyl-2-iodopropane, 2-iodoethanol, and mixtures thereof.

Representative examples of suitable Group III-b, IV-b, V-b and VI-b metal halides (according to the periodic chart of Cotton and Wilkinson "Advanced Inorganic Chemistry" [3rd ed. 1972]) referred to herein as Group 9 co-catalysts include halides of Al, Ga, In, Tl, Ge, Sn, Pb, P, Si, As, Sb, Bi, S, Se, Te, and Po.

Specific Group 9 metal halides include $AlCl_3$, $GaBr_3$, $TlCl_3$, $SiCl_4$, $SiBr_4$, $PI_3$, $PBr_3$, $SbF_5$, $SbBr_3$, $SbI_3$, $BiCl_3$, $BiBr_3$, $AsI_3$, $AsBr_3$, $AsCl_3$, $SeF_4$, $SeCl_4$, $SeBr_4$, $TeF_4$ and mixtures thereof.

Suitable halogen co-catalysts (referred to herein as Group 10 co-catalysts) include $F_2$, $Cl_2$, $Br_2$, and $I_2$.

Any of the co-catalysts described in each of the aforenoted Group 1 to 10 co-catalysts can be employed alone or in conjunction with one or more co-catalysts in the same group and/or with one or more of the co-catalysts in the remainder of said groups in any amounts effective to increase the rate and/or selectivity of the hydroxylation reaction relative to that observed in their absence.

Accordingly, while any effective amount of co-catalysts can be employed, it is contemplated that such effective amounts constitute typically from about 0.1 to about 10,000 mole percent, preferably from about 0.50 to about 1,000 mole percent, and most preferably from about 10 to about 500 mole percent, based on the total number of moles of osmium in the supported osmium catalyst employed.

Since the supported osmium catalyst will typically be employed as a fixed bed through which the reaction mixture containing the co-catalyst will be passed, the aforedescribed amounts of co-catalyst preferably are determined based on the volume of reaction mixture in contact with the fixed bed of supported osmium at any given time during the hydroxylation reaction (referred to herein as the "effective volume"), e.g., the aforedescribed mole percents are contained in the effective volume of the reaction mixture.

It is to be understood that while it is contemplated that co-catalyst will always be employed in conjunction with the supported osmium catalyst, it is also contemplated that the support itself can function as the co-catalyst, such as a support of magnesium oxide which acts in a manner similar to the Group 2 co-catalysts.

Preferred combinations of co-catalysts include the use of at least one Group 1 co-catalyst in combination with at least one co-catalyst falling within any one or more co-catalyst Groups 2–9 (e.g., Group 6 or Group 8).

The most preferred co-catalysts are those of Group 1 and/or Group 8.

Illustrative examples of suitable co-catalyst combinations include $CuBr_2$ and NaCl; $CuCl_2$ and NaBr; $FeCl_3$ and NaCl; $CuBr_2$ and tetraethyl ammonium chloride; $FeCl_2$ and KBr; $FeBr_3$ and CsCl; CuI and NaBr; and n-butyl iodide and NaI.

The oxidant which is employed to oxidize the olefin includes organic hydroperoxides, hydrogen peroxide, and oxygen (the term oxygen being defined herein to include oxygen alone or as an oxygen containing gas).

The preferred class of oxidants is the organohydroperoxides. Conventional organohydroperoxides include those having the formula:

$$R''OOH \qquad (VII)$$

wherein R'' is a substituted or unsubstituted: alkyl, typically about $C_3$ to about $C_{20}$, preferably about $C_3$ to about $C_{10}$, most preferably about $C_3$ to about $C_6$ alkyl; aryl, typically $C_6$ to $C_{14}$, preferably $C_6$ to $C_{10}$, most preferably $C_6$ aryl; aralkyl and alkaryl wherein the aryl and alkyl groups thereof are as defined immediately above; cycloalkyl, typically about $C_4$ to about $C_{20}$, preferably about $C_4$ to about $C_{10}$, most preferably about $C_4$ to about $C_8$ cycloalkyl; as well as oxacyclic having 1 to about 5 oxygens and preferably 3 to about 20 carbons, and azacyclic having 1 to about 5 nitrogens and preferably about 3 to about 20 carbons; and wherein the substituents of said R'' group include halogen, hydroxy, ester and ether groups.

Representative examples of suitable organohydroperoxides include ethylbenzyl hydroperoxide, t-butyl hydroperoxide, t-amyl hydroperoxide, cumene hydroperoxide, 2-methyl-2-hydroperoxy-methyl proprionate, 2-methyl-2-hydroperoxy propanoic acid, pyrrolehydroperoxide, furan hydroperoxide, 2-butylhydroperoxide, cyclohexyl hydroperoxide, and 1-phenyl-ethylhydroperoxide.

The most preferred organic hydroperoxides include t-butyl hydroperoxide, ethylbenzylhydroperoxide, and t-amyl hydroperoxide. Frequently these hydroperoxides are made by the molecular oxygen oxidation of the corresponding hydrocarbon which also produces an alcohol as a by-product. For example, when isobutane is oxidized with molecular oxygen there is produced tertiary butyl hydroperoxide and tertiary butyl alcohol. It is not necessary to separate the alcohol from the hydroperoxide since the alcohol can function as a diluent or solvent.

The amount of organohydroperoxide employed is not critical and can vary widely. Generally, the organohydroperoxide is employed in less than stoichiometric requirements, i.e., less than 1:1 molar ratio of organohydroperoxide per mole of ethylenic unsaturation in the olefin to be hydroxylated. Thus, while any amount of hydroperoxide effective to hydroxylate the olefin can be employed, it is contemplated that such effective amounts constitute a ratio of moles of ethylenic unsaturation in the olefin to moles or organohydroperoxide of from about 0.5:1 to about 100:1, preferably from about 1:1 to about 20:1 and most preferably from about 2:1 to about 10:1.

While the organohydroperoxide can be added to the reaction mixture in anhydrous form, it is also possible to add the organohydroperoxide as an aqueous solution comprising from about 1 to about 99%, preferably from about 10 to about 90%, and most preferably from about 20 to about 70%, by weight hydroperoxide, based on the weight of the aqueous hydroperoxide solution.

A suitable alternative oxidant is $H_2O_2$. The amount of $H_2O_2$ employed can vary over wide limits and can be any effective amount. Accordingly, effective molar ratios of olefin ethylenic unsaturation to $H_2O_2$ can vary from about 0.5:1 to about 100:1, preferably from about 1:1 to about 20:1, most preferably from about 2:1 to about 10:1.

The $H_2O_2$ can be employed in anhydrous form or as an aqueous solution. Such aqueous solutions typically will contain from about 3 to about 99.9%, preferably from about 20 to about 75%, and most preferably from about 20 to about 45% (e.g., 25 to 35%), by weight $H_2O_2$ based on the total weight of the aqueous solution.

If oxygen or an oxygen-containing gaseous mixture (e.g., containing one or more inert gases such as $N_2$ or air) is employed as the oxidant, it is preferred to also employ at least one Group 6 co-catalyst (described above) in conjunction therewith.

The molar ratio of oxygen to olefin ethylenic unsaturation also can vary widely but for safety reasons it is maintained outside explosive limits, said explosive limits usually being expressed as weight percent ratios.

For example, when hydroxylating ethylene or propylene, if oxygen is in excess, the ratio typically will be about 98 weight percent oxygen or more and 2 percent or less of the olefin based on the total weight of these two reactants. Alternatively, if the olefin is in large excess, the oxygen concentration typically will be about 10 weight percent and about 90 weight percent olefin. When oxygen is in excess, olefin can be added during the reaction as the reaction proceeds. On the other hand, where the olefin is in excess, oxygen can be added during the reaction as the oxygen is consumed.

It is also critical to have water present during the hydroxylation reaction since the water is believed to contribute one of the oxygen molecules constituting one of the hydroxyl groups in the resulting glycol. The source of this water is not critical. Thus, the water formed in-situ during the reaction between $H_2O_2$ and olefin can contribute to the water content for the reaction. Water can also be added separately, preferably as the solvent for the organohydroperoxide. Consequently, water is provided to, and/or is present, in the initial reaction mixture in at least a stoichiometric molar ratio with the molar amount of ethylenic unsaturation of the olefin to be hydroxylated. Such ratios preferably also are present in the reaction mixture at any given time after start-up. Accordingly, water is present in the reaction mixture at molar ratios of water to olefin ethylenic unsaturation to be hydroxylated in the reaction mixture of from about 1:1 to about 100:1, preferably from about 1:1 to about 50:1, and most preferably from about 1:1 to about 20:1. Such molar ratios typically can be achieved by controlling the amount of water in the reaction mixture (including water formed in-situ) to be from about 1 to about 90 percent, preferably from about 15 to about 85 percent, and most preferably from about 20 to about 60 percent, by weight, based on the total weight of the reaction mixture. Preferably the amount of water employed is less than that which will cause separation of the reaction mixture into an aqueous phase and organic phase although this is not a critical condition.

Olefins which can be hydroxylated in accordance with the present invention contain at least one ethylenic unsaturation and comprise any of the unsaturated aliphatic or alicyclic compounds well known in the art for undergoing such hydroxylation reactions. Typically, such compounds will contain from about 2 to about 20 carbons, preferably from about 2 to about 10 carbons, and most preferably from about 2 to about 5 carbons. Such compounds may be straight or branched chain, mono-olefinic, di-olefinic, or poly-olefinic, conjugated or non-conjugated. They may be substituted with such groups as aryl, preferably aryl of from 6 to about 14 carbons, alkyl, preferably alkyl of from 1 to 10 carbons, or aralkyl and alkaryl wherein the alkyl and aryl portions thereof are as described above, as well as with functional groups such as hydroxy, carboxyl and anhydride.

Typical of such olefins are those represented by the structural formula:

(VIII)

wherein $R_6$, $R_8$, and $R_9$, which may be the same or different, are selected from the group consisting of hydrogen; substituted or unsubstituted: alkyl, aryl, alkaryl, and aralkyl hydrocarbyl groups, said hydrocarbyl groups being preferably as defined immediately above; or any two or said $R_{7-9}$ groups together can constitute a cycloalkyl group typically of from about 4 to about 12, preferably from about 5 to about 8 carbons.

Representative olefins which can be hydroxylated and contain at least one ethylenic unsaturation include: ethylene, propylene, butene-1, butene-2, isobutene, butadiene, pentene-1, pentene-2, hexene, isohexene, heptene, 3-methylhexene, octene-1, isooctene, nonene, decene, dodecene, tridecene, pentadecene, octadecene, eicosene, docosene, tricosene, tetracosene, pentacosene, butadiene, pentadiene, hexadiene, octadiene, decadiene, tridecadiene, eicosadiene, tetracosadiene, cyclopentene, cyclohexene, cycloheptene, methylcyclohexene, isopropylcyclohexene, butylcyclohexene, oxtylcyclohexene, dodecyclohexene, acrolein, acrylic acid, 1,2,3,4-tetrahydrophthalic anhydride, methyl methacrylate, styrene, cholesterol and mixtures thereof.

The preferred olefins are ethylene, propylene, isobutylene, butadiene, styrene, allyl alcohol and allyl chloride.

The most preferred olefins are ethylene and propylene.

The preferred mode for conducting the hydroxylation reaction is to contact the supported osmium catalyst with a liquid reaction mixture, preferably provided as a homogeneous or substantially homogeneous medium and preferably but optionally by using an inert organic solvent to dissolve or assist in dissolving the co-catalysts and reactants.

Partial immiscibility of the solvent with water is acceptable although not preferred. By an inert solvent is meant one which does not undergo oxidation during the course of the reaction.

Suitable inert organic solvents should not dissolve either the support or the osmium compound adsorbed on the support under reaction conditions, and preferably possess polar functional groups and include aliphatic or aromatic alcohols having from 1 to about 10 carbon atoms, preferably tertiary alcohols, aliphatic or aromatic ketones having from 3 to about 10 carbon atoms, aliphatic or alicyclic ethers having from 2 to about 10 carbon atoms, glycols having from 2 to about 10 carbon atoms, N,N-dialkyl amides having from 3 to about 10 carbon atoms, nitriles having from about 2 to about 10 carbons, aliphatic or aromatic sulfoxides having from 2 to about 14 carbon atoms, aliphatic or aromatic sulfones having from 2 to about 14 carbon atoms, and the like. Examples of suitable solvents include methanol, ethanol, propanol, butanol, hexanol, decanol, t-butyl alcohol, t-amyl alcohol, benzyl alcohol, acetone, methylethyl ketone, methylbutyl ketone, acetophenone, ethylene glycol, propylene glycol, diethylene glycol, tetraethylene glycol, dimethyl formamide, diethyl formamide, dimethyl acetamide, dimethyl sulfoxide, diethyl sulfoxide, di-n-butyl sulfoxide, diphenyl sulfoxide, dibenzyl sulfoxide, dimethyl sulfone, diethyl sulfone, tetra methylene sulfone, diphenyl sulfone, acetonitrile, pyridine, dioxane, tetra hydrofuran, tetra hydropyran, dioxolane, and mixtures thereof.

The preferred solvents include those which are substantially or completely miscible with water such as t-butyl alcohol, methanol, and acetonitrile.

The most preferred solvent is the product alcohol derived from the organic hydroperoxide, or mixtures of the product glycol and the hydroperoxide derived product alcohol.

For example, when ethylene is hydroxylated using t-butyl hydroperoxide, the preferred solvent is t-butyl alcohol, or a mixture of ethylene glycol and t-butyl alcohol, the latter being formed in-situ from t-butyl hydroperoxide.

It is to be understood that when the osmium compound is chemically adsorbed by the support, i.e., undergoes a chemical reaction therewith, the solvent is selected so that it will not cause disassociation or displacement of the catalyst from the support. However, if the osmium compound is only physically adsorbed by the support, the solvent is selected so that the osmium compound is not soluble therein. Otherwise the solvent may dissolve the osmium compound from the support. In this instance, it is desirable to avoid the use of a solvent other than the product alcohols as described above. Furthermore, if the physically adsorbed osmium compound is soluble in any of the other components of the reaction mixture, it should not be used and a suitable chemically adsorbed supported catalyst should be employed instead.

Similar considerations apply with respect to the selection of a suitable co-catalyst for use in conjunction with a chemically adsorbed catalyst. For example, certain co-catalysts such as the Na, K, Rb, and Cs hydroxides can displace or leach osmium from certain supports, such as alumina, during the hydroxylation reaction. Accordingly, such specific combinations of supported osmium catalysts and co-catalysts should be avoided when one wishes to employ a completely heterogeneous osmium catalyst.

The inert solvent is preferably employed in amounts sufficient to achieve a homogeneous solution with respect to at least the olefin and oxidant. Typically such amounts can vary from about 0 to about 90 percent, preferably from about 20 to about 80 percent, and most preferably from about 20 to about 50 percent, by weight, based on the total weight of the reaction mixture.

The pH of the reaction mixture during the hydroxylation reaction need not be rigidly controlled although it will typically not be allowed to drop below about 4, preferably not below about 6. Likewise, the pH of the reaction mixture typically will not be allowed to exceed about 12 although the process can still be conducted at a pH below 4 and above 12. Accordingly, the pH of the reaction mixture typically will be maintained between 4 and 12, preferably between about 5 and about 12, and most preferably between about 6 and about 12. The pH of the reaction mixture can be controlled by the use of conventional buffers or base where needed. Preferably, pH control is achieved typically by the use of co-catalyst base or other basic material such as pyridine, or a buffer.

However, in the embodiment wherein $H_2O_2$ is employed as the oxidant in conjunction with a supported osmium halide or oxyhalide catalyst, it is essential to maintain the initial pH of the reaction mixture from neutral to basic, e.g., typically from about 7 to 14, preferably from about 7 to about 12, and most preferably from about 7 to about 10. Preferably, the pH is maintained at these levels throughout the reaction.

In carrying out the invention, olefin, water, oxidant, supported osmium catalyst, co-catalyst, and optional inert solvent are brought into contact in a manner and under conditions sufficient to hydroxylate the olefin, i.e., to convert at least one of the ethylenic unsaturations possessed thereby to its corresponding diol.

The hydroxylation reaction can be conducted using the supported osmium catalyst in fixed bed or slurry form. Either mode is preferably conducted by preparing a reaction mixture comprisng oxidant, co-catalyst, water and olefin. This reaction mixture will additionally comprise a suspension of the supported osmium catalyst when operating in the slurry mode.

The manner and order of mixing of each of the individual components of the liquid reaction mixture for either the fixed bed or slurry mode is not critical. However, when an organohydroperoxide is used as the oxidant, it is preferred in the slurry mode to mix the supported osmium catalyst, and co-catalyst with solvent, additional additives such as buffers, where needed, and then add the organic hydroperoxide and olefin.

Accordingly, the reaction mixture will typically comprise: (a) an organohydroperoxide in an amount of from about 1 to 70 percent, preferably from about 5 to about 60 percent, and most preferably from about 10 to about 50 percent, by weight, based on the weight of the reaction mixture exclusive of the weight of supported catalyst, co-catalyst and any other additive (e.g., buffers) if present; (b) supported osmium catalyst in amounts heretofore specified if operating in the slurry mode; (c) water subject, to the molar constraints heretofore specified, in an amount of from about 1 to about 98 percent, preferably from about 10 to about 80 percent, and most preferably from about 30 to about 60 percent, by weight, based on the total weight of the reaction mixture exclusive of the weight of supported catalyst, and any other additives (e.g., buffers) and co-catalysts; (d) inert organic solvent in an amount of from about 0 to about 99 percent, preferably from about 20 to about 80 percent, and most preferably from about 30 to about 60 percent, by weight, based on the weight of the reaction mixture exclusive of the weight of supported catalyst, other additives and co-catalyst; and (e) olefin in amounts hereinafter. specified. Co-catalysts are used in effective amounts as described above as are buffers to control pH where desired.

When an aqueous $H_2O_2$ solution (as defined above) is employed as the oxidant, it preferably will comprise from about 1 to about 70 percent, preferably from about 5 to about 60 percent, and most preferably from about 10 to about 50 percent, by weight, based on the weight of the reaction mixture exclusive of supported catalyst, other additives, and co-catalyst.

For the production of ethylene glycol, propylene glycol or any product derived from any unsaturated gaseous olefin by the slurry mode, the olefin, and oxygen if employed as an oxidant, may be bubbled through the reaction mixture containing the components described herein or it may be introduced under pressure.

However, it is preferred for either the fixed bed or slurry mode that the reaction takes place in the liquid phase. Consequently, sufficient pressure is preferably employed to maintain the gaseous reactants in the liquid phase. Otherwise, the reaction pressure is not critical and can be atmospheric, sub-atmospheric, or super-atmospheric.

When the olefin reactant is a liquid or is dissolved in the reaction mixture under pressure, its concentration in the reaction mixture typically will vary from about 1 to about 98 percent, preferably from about 10 to about 80 percent, and most preferably from about 10 to about 60 percent, by weight, based on the total weight of the reactant mixture inclusive of the weight of components (a) through (d) described above.

The hydroxylation reaction is typically conducted at temperatures which can vary over wide limits although it is preferred to maintain the reaction mixture in the liquid phase. Accordingly, typical reaction temperatures can vary from about 0° to about 250° C., preferably from about 20° to about 150° C., and most preferably from about 30° to about 130° C.

At temperatures greater than the aforenoted ranges, the reaction rate may increase substantially but this usually occurs at the expense of a significant reduction in selectivity. At very low reaction temperatures, e.g., below about 0° C. the reaction rate decreases to a commercially undesirable degree. Accordingly, while the reaction temperature is not critical and can vary over a wide range, one normally would not operate at temperature extremes outside the aforenoted ranges.

In the preferred fixed bed mode, the liquid reaction mixture, preferably a homogeneous reaction mixture, is prepared comprising oxidant, co-catalyst, water and olefin and the reaction mixture is passed, preferably continuously, through a fixed bed reactor containing the supported catalyst at reaction temperature and at a rate such that substantially complete reaction will have taken place by the time the reaction mixture reaches the reactor outlet.

A variety of fixed bed reactors will be found to be useful and multiple tube heat exchanger type of reactors are satisfactory.

In the slurry mode, a reaction mixture containing the above described components and suspended supported osmium catalyst is charged into a reactor vessel along with olefin. The reaction is allowed to proceed to completion, typically for a period of from about 0.5 to about 24 hours, preferably from about 0.5 to about 12 hours, and most preferably from about 0.5 to about 2 hours.

In a continuous slurry mode, the reaction mixture components can be introduced into the inlet of an elongated reactor adapted to retain, e.g., by filtration, the slurried supported catalyst at a rate such that substantially complete reaction will have taken place by the time the reaction mixture reaches the reactor outlet. The slurry mode can also be carried out in a semi-continuous manner by metering the reactant mixture components into a series of two or more tank reactors adapted as described above at the appropriate rate to maintain the reactor liquid level.

Additionally, the process may be run in either of the aforementioned modes by altering the reaction conditions, and/or, the reactant, solvent, catalyst, co-catalyst, and pH control additive concentrations during the course of the reaction. Thus, the process may be run by changing the temperature, pressure, catalyst concentration, oxidant concentration, and/or olefin concentration.

While it is preferred to conduct the hydroxylation reaction with the reactants in the liquid phase, it is contemplated that when oxygen or oxygen-containing gas is employed as an oxidant, the hydroxylation reaction can be conducted with the reactants in the vapor phase as they contact the supported osmium catalyst, provided, however, that at least one of the Group 6 co-catalysts described herein is also deposited on the support.

In either fixed bed or slurry mode, the spent reaction mixture after removal of unreacted olefin is a solution of product glycol, product alcohol derived from the organic hydroperoxide if used, by-products if any, solvent, water, and co-catalyst (if the co-catalyst is soluble in the reaction mixture).

The reaction mixture is then distilled to separate product(s) and by-products, if any, from the co-catalyst which is recycled.

Thus, the use of a supported catalyst enables the process to be conducted by retaining the expensive and toxic osmium catalyst in the hydroxylation reactor and avoids the necessity of carrying the osmium catalyst through the downstream processing steps where product separation takes place. This eliminates loss of osmium and other problems associated with leaks in equipment downstream of the hydroxylation reactor.

The following examples are given as specific illustrations of the claimed invention. It should be understood, however, that the invention is not limited to the specific details set forth in the examples. All parts and percentages in the examples as well as in the remainder of the specification are by weight unless otherwise specified.

While many of the following examples may be written in the present tense, it is to be understood that such examples represent work actually performed.

Unless otherwise specified, in the following examples selectivity, conversion and yield are calculated as follows:

$$\% \text{ selectivity} = \frac{\text{moles of glycol formed}}{\text{moles of oxidant consumed}} \times 100$$

$$\% \text{ conversion} = \frac{\text{moles of oxidant consumed}}{\text{moles of oxidant charged}} \times 100$$

$$\% \text{ yield} = \% \text{ conversion} \times \% \text{ selectivity}$$

EXAMPLE 1

The following example illustrates the preparation of an $Os_3(CO)_{12}$ catalyst supported with MgO.

Into a reaction vessel is charged 100 g of cyclohexane, 5 g of magnesium oxide powder, obtained from Alfa Products, and 0.050 g of $Os_3(CO)_{12}$ at room temperature to produce a standard solution of the osmium carbonyl. The resulting mixture is stirred overnight, i.e., 18 to 20 hours, at room temperature. The mixture is then filtered and the recovered solids rinsed 3 times with methylene chloride.

EXAMPLE 2

The following example illustrates the preparation of an osmium carbonyl catalyst supported with $Al_2O_3$.

The method of preparation is described by Deeba, M., and Gates, B. C., 67 J. of Catalysis, 302–303 (1981) and the supported catalyst was obtained from Professor Gates, the co-author of this article.

More specifically, and in accordance with the above article, a solution of n-octane containing $Os_3(CO)_{12}$ dissolved therein and gamma-alumina (surface area 185 $m^2/g$) suspended therein is refluxed. The alumina support, however, is dehydroxylated by contacting it with flowing $N_2$ gas at 300° C. prior to introducing it into the n-octane solution.

EXAMPLE 3

An osmium carbonyl on $Al_2O_3$ is prepared as follows:

Osmium carbonyl, 0.33 g $Os_3(CO)_{12}$, is charged to a flask and partially dissolved in 250 ml of heptane at 95° C. To this partial solution is added 30 g of ⅛" diameter alumina spheres. The flask is then rotated in a water bath at 100° C. for 6 hours, after which time the yellow solution had turned colorless. As much as possible of the liquid and the suspended alumina powder is removed by decanting. The solids remaining in the flask after decanting are rinsed with heptane and decanted again. The supported catalyst is also washed 3 times with 50 ml of methylene chloride to remove any non-chemically bonded osmium compound, and dried in vacuo at room temperature.

EXAMPLE 4

As osmium carbonyl, on magnesia support, is prepared in accordance with the procedure of Example 3, using 0.16 g $Os_3(CO)_{12}$, 150 ml of heptane, and 30 g of ⅛" diameter magnesia pellets.

EXAMPLE 5A

Carbon chips having 1% by weight osmium metal deposited on the surface thereof, based on the weight of osmium and carbon, were obtained from Engelhard Industries Inc.

EXAMPLE 5B

Silica (SiO$_2$) chips having 1% by weight osmium deposited thereon, based on the weight of osmium and silica, were obtained from Engelhard Industries, Inc.

EXAMPLE 5C

An alumina (Al$_2$O$_3$) support having 5% by weight osmium metal deposited thereon, based on the weight of osmium and alumina was obtained from K and K Laboratories under the tradename "5% Osmium on Aluminum" [SIC].

EXAMPLE 6

A mixture of 40.98 grams of tertiary-butanol, 10.00 grams of 90% tertiary-butylhydroperoxide (100 mmoles) in water, 2.32 grams of 3-ethyl-3-pentanol internal standard, and 6.70 grams of water, is heated in a reaction vessel to 70° C., pressurized with ethylene to 700 psig and circulated at a rate of 12 to 60 ml/min through a stainless steel tube, 12"×0.5" o.d., stoppered at the bottom with a plug of glass wool, and containing 15.0 grams of the osmium carbonyl on magnesia catalyst, prepared in accordance with Example 4, for 50 minutes. After cooling to 40° C., venting excess ethylene, and discharging the reaction mixture into a bottle, analysis of the reaction mixture by gas liquid chromatography (GLC) shows the formation of 50 mmoles of ethylene glycol. The results are summarized at Table 1.

This example illustrates the efficiency of a basic support, such as magnesium oxide wherein the support itself functions as a co-catalyst.

EXAMPLE 7

Into a 100 ml 3-neck flask provided with condenser, addition funnel, and magnetic stirrer is charged t-butylalcohol (20.0 g), 1-octene (4.48 g), water (1.0 g), NaI (0.03 g) and 0.30 g of the Os(CO)$_{12}$/MgO supported catalyst prepared in accordance with Example 1. At ambient temperature (26° C.), 2.0 g of a solution of 90% by weight, tertiary butyl hydroperoxide dissolved in t-butyl alcohol is added dropwise over a period of 2 minutes with stirring. After 12 hours from completion of the addition, the reaction mixture is analyzed by GLC and complete conversion of the hydroperoxide is obtained with a selectivity to 1,2-octanediol of 84%. The results are summarized at Table 1.

EXAMPLE 8

A mixture of Os$_3$(CO)$_{12}$/Al$_2$O$_3$ (0.2 g) obtained from Example 2, t-butyl alcohol (i.e., TBA) (20.0 g), water (1.0 g), sodium iodide (0.03 g), and 1-octene (4.48 g) is charged into a 100 ml 3-neck flask provided with condenser, addition funnel, and magnetic stirrer. At ambient temperature (26° C.), tertiary butyl hydroperoxide (2.0 g., 90% in TBA) is added slowly with stirring over 2 minutes dropwise. After 12 hours, complete conversion of the hydroperoxide is obtained with selectivity to the 1,2-octanediol of 51%. About 35% ketol is also produced which is also a saleable by-product. The results are summarized in Table 1.

EXAMPLES 9 TO 12

Four glass bottles, each containing a magnetic stirring bar, are charged at 0° C. with the following, in the order listed:

(i) 0.5 g of 5% osmium on alumina catalyst (provided from Example 5C);

(ii) 1.0 g of an aqueous solution containing 0.1 mmole of a co-catalyst, listed in Table A;

(iii) 42.0 grams of a stock solution of isobutene in aqueous t-butyl alcohol, said stock solution having a composition by weight as follows: t-butyl alcohol (76.1%), isobutene (14.4%), and water (9.5%);

(iv) 1.28 g (10.0 mmoles) of a solution containing 70%, by weight, tertiary-butylhydroperoxide in water.

The bottles are capped tightly and the mixtures stirred at room temperature for 18–20 hours. After uncapping, stirring is continued until isobutene is no longer evolved, and 1.11 g of tetraglyme internal standard are added. The mixtures are filtered to remove the catalyst and analyzed by GLC, which shows the formation of isobutylene glycol in the amounts shown at Table A. The results are further summarized in Table 1.

TABLE A

| Example No. | Co-Catalyst | Isobutylene Glycol (mmoles) |
|---|---|---|
| 9 | NaI | 9.3 |
| 10 | NaOH | 8.4 |
| 11 | NaO$_2$CCH$_3$ | 5.0 |
| 12 | None | 2.3 |

In addition, the filtered reaction mixture from Example 9 is analyzed by X-ray fluorescence spectroscopy, which shows the absence of osmium therein (limit of detectability is 2 ppm). However, Os is detected in the filtrate of Example 10 employing NaOH. These examples illustrate the advantage of using a co-catalyst, and the superior efficacy of sodium iodide in this role. The lack of detectable osmium in the filtered reaction mixture in Example 9 also illustrates that the catalyst is not removed from the support during reaction. However, the leaching of Os in Example 10 indicates that the particular combination of co-catalyst support and osmium compound is best avoided.

EXAMPLE 13

The filtered catalyst from Example 9 is charged to a glass bottle, followed by 1.0 gram of water, 42.0 grams of the stock solution of isobutene used in Examples 9 to 12 and 1.28 g of 70% tertiary-butylhydroperoxide in water. This mixture is treated as described in Examples 9 to 12. Analysis shows the formation of 3.1 mmoles of isobutylene glycol. The results are also summarized in Table 1.

This Example illustrates the fact that the iodide ion of the co-catalyst is not adsorbed onto this particular supported catalyst and must be added with the reagents if its presence is desired.

EXAMPLE 14

Example 13 is repeated with the exception that 1.0 g of a 1.5%, by weight, solution of NaI in water is added to the filtered catalyst in addition to the other reagents recited in Example 13. The hydroxylation reaction and analysis is conducted in accordance with the procedures of Example 9. This analysis shows 7.9 mmoles of isobutylene glycol and the absence of detectable osmium in the filtered reaction mixture. The results are also summarized at Table 1.

EXAMPLE 15

A glass bottle, containing a magnetic stirring bar is charged with 8.0 g of 90% tertiary-butylhydroperoxide (balance is 5% t-butyl alcohol and 5% water), 35.2 g of t-butyl alcohol, 26.5 g of water, 2.0 g of an aqueous 3% sodium iodide solution, 168.0 g of the stock solution of isobutene used in Examples 9 to 12, and 0.32 g of 5% osmium on alumina obtained as in Example 5C. The bottle is capped and the mixture stirred at room temperature overnight (18-20 hours). The cap is removed and the mixture stirred until no more isobutene is evolved. The mixture is filtered free of catalyst. The catalyst is washed with 20 ml of 90% (by volume) t-butyl alcohol in water. The filtrate and washings are combined to give 209.2 g of clear colorless liquid. A sample of the liquid (16.8 g) is retained for osmium analysis and the remainder is distilled at atmospheric pressure to give 180.0 g of aqueous t-butyl alcohol (bp. 78°-9° C.) and then in-vacuo to give 5.0 g of isobutylene glycol [bp. 45°-6° C. (0.1 mm)]. The glycol is identified by its proton NMR spectrum in CDCl$_3$ solution, which shows singlet resonances at 1.17 (6H, methyl groups), 3.37 (2H, methylene group), and 4.12 (2H, hydroxyl groups) ppm downfield from internal tetramethylsilane reference. In this Example selectivity is based on the moles of glycol actually recovered by distillation the identity of which is confirmed by spectroscopy. Analysis for osmium shows that none is present in the retained sample of the reaction mixture or in the aqueous tertiary-butanol and isobutylene glycol distillates, subject to a detectability limit of 2 ppm, thereby illustrating that no volatile osmium species is formed or present in the tested liquid media. Conversion and selectivity results are summarized at Table 1.

EXAMPLES 16 TO 19

A 12" by ½" o.d. tube stoppered with glass wool and connected in series with a 300 ml titanium autoclave is filled with a different supported catalyst for each of Examples 16 to 19, the identity and weight of each supported catalyst being summarized at Table B. For each example, the titanium autoclave is charged with a mixture of 40.83 g of t-butyl alcohol, 10.00 g of 90% tertiary-butylhydroperoxide (100 mmoles) in water, and 2.32 g of 3-ethyl-3-pentanol internal standard. The mixture is heated to 70° C. and the autoclave pressurized with ethylene to 700 psig. A solution of 0.15 g of NaI in 6.60 g of water is then charged to the autoclave. The resulting mixture is circulated continuously from the autoclave through the fixed bed of catalyst, and back to autoclave again at a rate of 12 to 20 ml/min. After the reaction times shown in Table B, the reaction mixture is cooled to 40° C., the excess ethylene is vented and the autoclave contents are discharged into a serum capped bottle. Gas liquid chromatographic examination of reaction mixtures obtained shows the formation of ethylene glycol as indicated in Table B. The results in terms of conversion and selectivity are summarized at Table 1. These examples illustrate that a continuous fixed bed process can be employed using the supported catalyst and co-catalyst described herein.

TABLE B

| Ex. No. | Supported Catalyst | Supported Catalyst Source Ex. No. | Weight of Supported Catalyst (g) | Reaction Time (min.) | Ethylene Glycol Formed (mmoles) |
|---|---|---|---|---|---|
| 16 | 1% Os/C | 5a | 5.0 | 65 | 36 |
| 17 | 1% Os/SiO$_2$ | 5b | 5.0 | 95 | 59 |
| 18 | Os$_3$(CO)$_{12}$/Al$_2$O$_3$ | 3 | 10.0 | 30 | 58 |
| 19 | Os$_3$(CO)$_{12}$/MgO | 4 | 15.0 | 120 | 71 |

EXAMPLES 20 TO 25

The osmium carbonyl on alumina catalyst used in Example 18 is left in the fixed bed tube and reused for the conversion of six further batches of reaction mixture (designated as Examples 20 to 25) in the same manner as Example 18. The quantities of t-butyl alcohol, tertiary-butylhydroperoxide, 3-ethyl-3-pentanol, sodium iodide, and water, for each batch are the same as in Example 18, as are: circulation rate; reaction temperature and pressure. The reaction times are summarized at Table 1. The quantities of ethylene glycol formed are as shown in Table C. The results in terms of conversion and selectivity are summarized at Table 1.

TABLE C

| Example No. | Ethylene Glycol Formed (mmoles) | |
|---|---|---|
| 20 | 65 | 1st reuse of Os$_3$(CO)$_{12}$/Al$_2$O$_3$ |
| 21 | 56 | 2nd reuse of Os$_3$(CO)$_{12}$/Al$_2$O$_3$ |
| 22 | 64 | 3rd reuse of Os$_3$(CO)$_{12}$/Al$_2$O$_3$ |
| 23 | 63 | 4th reuse of Os$_3$(CO)$_{12}$/Al$_2$O$_3$ |
| 24 | 65 | 5th reuse of Os$_3$(CO)$_{12}$/Al$_2$O$_3$ |
| 25 | 67 | 6th reuse of Os$_3$(CO)$_{12}$/Al$_2$O$_3$ |

These examples illustrate the reusability of the supported catalyst in a fixed bed continuous process.

EXAMPLES 26 AND 27

These examples are intended to illustrate a supported catalyst wherein the support not only supports the osmium catalyst but also the promoter.

PART A

A strong base ion exchange resin Amberlite IRA-400 (OH$^-$) 50 ml (70 meq.) is added to 200 g of a 9% solution of HI acid in water and stirred for 18-20 hours. This converts the OH$^-$ counter ions on the resin to I$^-$ groups thereby producing IRA-400 (I$^-$). This procedure is repeated using HBr acid in place of HI to form IRA-400 (Br$^-$). The two halogenated supports are filtered to remove liquid, washed with water, and dried in-vacuo for 18 hours. The halide ion content of IRA-400 (Br$^-$) and IRA-400 (I$^-$) is determined and reported in Table D.

PART B

Osmium tetroxide is adsorbed onto the aforedescribed halogenated resins by stirring 1.0 g of each resin with 0.20 g of 2.5% osmium tetroxide in t-butyl alcohol and 42.0 grams of the stock solution of isobutene, used in Examples 9 to 12, for 2 days in tightly capped bottles at room temperature. The bottles and contents are cooled to −5° C. and 1.28 g of 70% tertiary-butylhydroperoxide in water are added to each. The bottles are recapped and the contents stirred at room temperature overnight (16-20 hours). After evaporation of isobutene, and addition of 1.11 g of tetraglyme internal standard and filtration, GLC analysis shows the quantities of isobutylene glycol reported in Table D. The results in terms of conversion and selectivity are reported in Table 1.

TABLE D

| Example No. | Resin | Resin Halide Analysis (meq/g) | Isobutylene Glycol Formed (mmoles) |
|---|---|---|---|
| 26 | IRA-400 (I$^-$) | 2.3 | 9.3 |
| 27 | IRA-400 (Br$^-$) | 2.2 | 2.0 |

EXAMPLES 28-30

The filtered resin catalyst from Example 26 is placed in a glass bottle, followed by 42.0 g of the isobutene stock solution used in Examples 9 to 12 and 1.28 g of 70% tertiary-butylhydroperoxide in water. The bottle is capped and the contents magnetically stirred at room temperature. The isobutene is allowed to evaporate, 1.11 g of tetraglyme internal standard are added, and the mixture is filtered. The residue of resin catalyst is used again under the same reaction conditions and then the whole process is repeated once more. Analysis of the filtrates from the three reaction mixtures obtained, shows the formation of the amounts of isobutylene glycol reported in Table E. The results in terms of conversion and selectivity are reported in Table 1. These examples illustrate the reusability of the resin supported catalyst.

TABLE E

| Example No. | | Isobutylene Glycol Formed (mmoles) |
|---|---|---|
| 28 | IRA-400 (I$^-$) first reuse | 9.2 |
| 29 | IRA-400 (I$^-$) second reuse | 9.5 |
| 30 | IRA-400 (I$^-$) third reuse | 9.4 |

COMPARATIVE EXAMPLE 1

Example 7 is repeated with the exception that the osmium carbonyl catalyst is omitted from the MgO support. No reaction occurs after 12 hours.

COMPARATIVE EXAMPLE 2

This example is intended to illustrate that the catalytic effect exerted by the osmium containing catalyst is due to the supported osmium and not an unsupported osmium species in the reaction mixture.

Accordingly, Example 9 is repeated and the reaction mixture is filtered to remove the supported catalyst. The resulting liquid filtrate is analyzed and found to contain 8.6 mmoles of isobutylene glycol. The liquid filtrate is cooled to $-5°$ C. and isobutene is bubbled into the chilled solution until a weight increase of 5.2 g has been achieved. To this solution, is added 1.0 g of aqueous 1.5% sodium iodide solution, and 1.28 g of 70% tertiary-butylhydroperoxide in water, but no source of osmium. After stirring overnight at room temperature, followed by venting of isobutene at room temperature, the solution is found to contain no isobutylene glycol additional to that which was initially present at the start of the reaction. Thus, it is concluded, that an unsupported dissolved osmium containing catalyst was absent in the filtrate recovered from Example 9, and that the glycol formulation of Example 9 was catalyzed by the supported catalyst.

TABLE I

| Example No. | Catalyst Type | Support Type | Reference Ex. No. for Preparing or Obtaining Supported Cat. | Amt. of Supported Cat. (g) | Oxidant Type | Oxidant Amount (g) | Olefin Type | Olefin Amount | Co-catalyst Type | Co-catalyst Amount | Solvent Type | Solvent Amount (g) | Reaction Conditions Temp. °C | Reaction Conditions Time | Conversion % | Diol Selectivity % | Comments |
|---|---|---|---|---|---|---|---|---|---|---|---|---|---|---|---|---|---|
| 6 | Os(CO)12 | MgO | 4 | 15.0 | TBHPA 90% | 10 g | Ethylene | 700 psig | None | N.A. | TBA | 40.98 | 70 | 50 min. | 100 | 50 | No Co-Catalyst used. |
| 7 | Os(CO)12 | MgO | 1 | 0.03 | TBHPA 90% | 2.0 | 1-Octene | 4.48 g | NaI | 0.03 g | TBA | 20.0 | 26 | 12 hr. | 100 | 84 | |
| 8 | Os(CO)12 | Al2O3 | 2 | 0.2 | TBHPA 90% | 2.0 | 1-Octene | 4.48 g | NaI | 0.03 g | TBA | 20.0 | 26 | 12 hr. | 100 | 51 | 35% Ketol is also produced Examples 9-12 vary type of Co-Catalyst |
| 9 | Os | Al2O3 | 5c | 0.5 | TBHPW 70% | 1.28 g | Isobutene | 5.92 g | NaI | 0.1 m moles | TBA | 32.0 | 26 | 18-20 hrs. | 100 | 93 | |
| 10 | Os | Al2O3 | 5c | 0.5 | TBHPW 70% | 1.28 g | Isobutene | 5.92 g | NaOH | 0.1 m moles | TBA | 32.0 | 26 | 18-20 hrs. | 100 | 84 | |
| 11 | Os | Al2O3 | 5c | 0.5 | TBHPW 70% | 1.28 g | Isobutene | 5.92 g | NaO2CCH3 | 0.1 m moles | TBA | 32.0 | 26 | 18-20 hrs. | 100 | 50 | |
| 12 | Os | Al2O3 | 5c | 0.5 | TBHPW 70% | 1.28 g | Isobutene | 5.92 g | None | None | TBA | 32.0 | 26 | 18-20 hrs. | 100 | 23 | |
| 13 | Os | Al2O3 | 5c | 0.5 | TBHPW 70% | 1.28 | Isobutene | 5.92 g | None added | None | TBA | 32.0 | 26 | 50 min. | 100 | 31 | Recycled filtered catalyst from Ex 9 has not adsorbed iodide ion. |
| 14 | Cat. recovered from Ex 9 | Al2O3 | | 0.5 | TBHPW 70% | 1.28 | Isobutene | 5.92 g | NaI | .015 g | TBA | 32.0 | 26 | 50 min. | 100 | 79 | This example shows reuseability of supported catalyst in Presence of Co-Catalyst |
| 15 | Cat. recovered from Ex 9 | Al2O3 | | 0.32 | TBHPA 90% | 8.0 | Isobutene | 23.7 g | NaI | 0.6 g | TBA | 163.2 | 26 | 18-20 hrs | 100 | 70 | Examples 16 to 19 employ continuous recycle of reaction mixture through bed of supported catalyst |
| 16 | Os | Carbon | 5a | 5 | TBHPA 90% | 10 | Ethylene | 700 psig | NaI | 0.15 g | TBA | 40.83 | 70° C. | 65 min. | 100 | 36 | |
| 17 | Os | SiO2 | 5b | 5 | TBHPA 90% | 10 | Ethylene | 700 psig | NaI | 0.15 g | TBA | 40.83 | 70° C. | 95 min. | 100 | 59 | |
| 18 | Os3(CO)12 | Al2O3 | 3 | 10 | TBHPA 90% | 10 | Ethylene | 700 psig | NaI | 0.15 g | TBA | 40.83 | 70° C. | 30 min. | 100 | 58 | |
| 19 | Os3(CO)12 | MgO | 4 | 15 | TBHPA 90% | 10 | Ethylene | 700 psig | NaI | 0.15 g | TBA | 40.83 | 70° C. | 120 min. | 100 | 71 | |
| 20 | Os3(CO)12 | Al2O3 | 3 | 10 | TBHPA 90% | 10 | Ethylene | 700 psig | NaI | 0.15 g | TBA | 40.83 | 70° C. | 35 min. | 100 | 65 | First recycle using supported catalyst from Ex. 18 |

TABLE I-continued

| Example No. | Catalyst Type | Support Type | Reference Ex. No. for Preparing or Obtaining Supported Cat. | Amt. of Supported Cat. (g) | Oxidant Type | Oxidant Amount (g) | Olefin Type | Olefin Amount | Co-catalyst Type | Co-catalyst Amount | Solvent Type | Solvent Amount (g) | Reaction Conditions Temp. °C | Reaction Conditions Time | Conversion % | Diol Selectivity % | Comments |
|---|---|---|---|---|---|---|---|---|---|---|---|---|---|---|---|---|---|
| 21 | Os$_3$(CO)$_{12}$ | Al$_2$O$_3$ | 3 | 10 | TBHPA 90% | 10 | Ethylene | 700 psig | NaI | 0.15 g | TBA | 40.83 | 70° C. | 60 min. | 100 | 56 | 2nd recycle |
| 22 | Os$_3$(CO)$_{12}$ | Al$_2$O$_3$ | 3 | 10 | TBHPA 90% | 10 | Ethylene | 700 psig | NaI | 0.15 g | TBA | 40.83 | 70° C. | 60 min. | 100 | 64 | 3rd recycle |
| 23 | Os$_3$(CO)$_{12}$ | Al$_2$O$_3$ | 3 | 10 | TBHPA 90% | 10 | Ethylene | 700 psig | NaI | 0.15 g | TBA | 40.83 | 70° C. | 80 min. | 100 | 63 | 4th recycle |
| 24 | Os$_3$(CO)$_{12}$ | Al$_2$O$_3$ | 3 | 10 | TBHPA 90% | 10 | Ethylene | 700 psig | NaI | 0.15 g | TBA | 40.83 | 70° C. | 75 min. | 100 | 65 | 5th recycle |
| 25 | Os$_3$(CO)$_{12}$ | Al$_2$O$_3$ | 3 | 10 | TBHPA 90% | 10 | Ethylene | 700 psig | NaI | 0.15 g | TBA | 40.83 | 70° C. | 80 min. | 100 | 67 | 6th recycle |
| 26 | OsO$_4$ | IRA-400 (I$^-$) | 26 | 1.005 | TBHPW 70% | 1.28 | Isobutene | 5.92 g | I$^-$ | 2.3 meq/g resin | TBA | 32.19 | 26 | 18–20 hrs. | 100 | 93 | Resin support contains catalyst and Co-catalyst halide ion in Examples 26 & 27 |
| 27 | OsO$_4$ | IRA-400 (Br$^-$) | 27 | 1.005 | TBHPW 70% | 1.28 | Isobutene | 5.92 g | Br$^-$ | 2.2 meq/g resin | TBA | 32.19 | 26 | 18–20 hrs. | 100 | 20 | |
| 28 | OsO$_4$ | IRA-400 (I$^-$) | 26 | 1.005 | TBHPW 70% | 1.28 | Isobutene | 5.92 g | I$^-$ | 2.3 meq/g resin | TBA | 32 | 26 | 18–20 hrs. | 100 | 92 | Exs. 28–30 successively reuse supported catalyst from Example 26 |
| 29 | OsO$_4$ | IRA-400 (I$^-$) | 26 | 1.005 | TBHPW 70% | 1.28 | Isobutene | 5.92 g | I$^-$ | 2.3 meq/g resin | TBA | 32 | 26 | 18–20 hrs. | 100 | 95 | |
| 30 | OsO$_4$ | IRA-400 (I$^-$) | 26 | 1.005 | TBHPW 70% | 1.28 | Isobutene | 5.92 g | I$^-$ | 2.3 meq/g resin | TBA | 32 | 26 | 18–20 hrs. | 100 | 94 | |

TBHPW = Tert butyl hydro peroxide in water
TBHPA = Tert butyl hydro peroxide in t-butylalcohol
TBA = t-butyl alcohol The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for hydroxylating olefins which comprises reacting in admixture at least one olefinic compound having at least one ethylenic unsaturation, with water and an oxidant selected from the group consisting of organic hydroperoxide, $H_2O_2$, and oxygen, in the presence of a catalyst composition under conditions and in a manner sufficient to convert at least one of said ethylenic unsaturation to its corresponding diol, said catalyst composition comprising:
(a) at least one osmium compound adsorbed on at least one support to form a supported osmium catalyst, said osmium compound being capable of catalyzing said hydroxylation reaction when adsorbed on said support, said supported osmium catalyst being insoluble in said admixture under hydroxylation reaction conditions; and optionally
(b) at least one co-catalyst capable of increasing at least one of the rate and selectivity of the hydroxylation reaction to product diol relative to the rate and selectivity in the absence of said co-catalyst.

2. The process of claim 1 wherein the osmium compound which is adsorbed of said support is selected from the group consisting of osmium carbonyls, osmium metal, halogenated osmium compounds, osmium oxides, ionic osmium compounds and osmium complexes.

3. The process of claim 2 wherein the osmium compound which is adsorbed on said support is at least one osmium carbonyl selected from the group consisting of $Os(CO)_5$, $Os_2(CO)_9$, $Os_3(CO)_{12}$, $Os_5(CO)_{16}$, $Os_6(CO)_{18}$, $Os_7(CO)_{21}$, and $Os_8(CO)_{23}$.

4. The process of claim 3 wherein the osmium carbonyl is $Os_3(CO)_{12}$.

5. The process of claim 3 wherein the osmium carbonyl is $Os(CO)_5$.

6. The process of claim 3 wherein the osmium carbonyl is $Os_2(CO)_9$.

7. The process of claim 2 wherein the osmium compound which is adsorbed on said support is represented by the structural formula selected from the group consisting of $Os(X)_n$, $Os(OH)X_3$, $OsOX_4$, $OsO_3X_2$, $OsONX_4$, $(M)_n$, $[OsX_6]^{-2}$, $(M)_n$, $[OsO_2X_4]^{-2}$, $M^{+1}[Os(OH)X_5]^{-1}$, $(M)_n$, $[OsO_4X_2]^{-2}$, $(M)_n$, $[OsO_2(OH)X_2]^{-2}$, $(M)_n$, $[OsNX_5]^{-2}$, and mixtures thereof, wherein said structural formulae: X is at least one halide independently selected from the group consisting of F, Cl, Br, and I; n is an integer from 1 to 6, M is selected from the group consisting of cations of Li, Na, K, Rb, Cs, Fr, Be, Mg, Ca, Sr, Ba, Ra, $NH_4$, tetra hydrocarbyl ammonium, and tetra hydrocarbyl phosphonium; and n' is a number selected in conjunction with the valence of cation M to achieve a neutral complex.

8. The process of claim 7 wherein the halogenated osmium compound is represented by the structural formula $OsX_3$.

9. The process of claim 7 wherein the halogenated osmium compound is represented by the structural formula $OsX_4$.

10. The process of claim 7 wherein the halogenated osmium compound is represented by the structural formula $OsX_5$.

11. The process of claim 7 wherein the halogenated osmium compound is represented by the structural formula $Os(OH)X_3$.

12. The process of claim 7 wherein the halogenated osmium compound is represented by the structural formula $OsOX_4$.

13. The process of claim 7 wherein the halogenated osmium compound is represented by the structural formula $OsO_3X_2$.

14. The process of claim 7 wherein the halogenated osmium compound is represented by the structural formula $OsONX_4$.

15. The process of claim 7 wherein the halogenated osmium compound is represented by the structural formula $(M)_n$, $[OsX_6]^{-2}$.

16. The process of claim 7 wherein the halogenated osmium compound is represented by the structural formula $(M)_n$, $[OsO_2X_4]^{-2}$.

17. The process of claim 7 wherein the halogenated osmium compound is represented by the structural formula $M^{+1}[Os(OH)X_5]^{-1}$.

18. The process of claim 7 wherein the halogenated osmium compound is represented by the structural formula $(M)_n$, $[OsO_4X_2]^{-2}$.

19. The process of claim 7 wherein the halogenated osmium compound is represented by the structural formula $(M)_n$, $[OsO_2(OH)X_2]^{-2}$.

20. The process of claim 7 wherein the halogenated osmium compound is represented by the structural formula $(M)_n$, $[OsNX_5]^{-2}$.

21. The process of claim 7 wherein the halogenated osmium compound is selected from at least one member of the group consisting of $OsF_3$, $OsCl_3$, $OsBr_3$, and $OsI_3$.

22. The process of claim 7 wherein M is a cation represented by the structural formula selected from the group consisting of $(R)_4N^+$, and $(R)_4P^+$ wherein R is a hydrocarbyl group selected from the group consisting of alkyl, aryl, aralkyl and alkaryl.

23. The process of claim 2 wherein the osmium compound which is adsorbed on said support is at least one osmium oxide selected from the group consisting of $OsO_2$, $OsO_3$, and $OsO_4$.

24. The process of claim 2 wherein the osmium compound which is adsorbed on said support is at least one ionic osmium compound represented by the structural formula:

$$M'_xOsO_y$$

wherein M' is a cation of a member selected from the group consisting of alkali metal, alkaline earth metal, ammonium, and tetra alkyl ammonium; x and y are numbers such that 2x-y is the valence of the osmium in any compound defined by this formula.

25. The process of claim 24 wherein the ionic osmium compound is represented by the structural formula $M'_2OsO_5$, $M'_2OsO_4$, $M'_2OsO_3$, $M'OsO_2$ and mixtures thereof.

26. The process of claim 25 wherein the ionic osmium compound is represented by the structural formula $M'_2OsO_5$.

27. The process of claim 2 wherein the osmium compound which is adsorbed on said support is an osmium complex wherein the ligand of the complex is selected from at least one member of the group consisting of (CO), PR₃, pi-bonded cyclopentadienyl, amine, and nitride.

28. The process of claim 27 wherein the osmium complex is represented by the structural formula selected from the group consisting of [Os(CO)X₅]⁻²; [Os(CO)₂X₄]⁻²; [Os(CO)₄X₂]⁻²; and [Os(CO)₃X₃]⁻¹ wherein X is a halide.

29. The process of claim 27 wherein the osmium complex is represented by the structural formula:

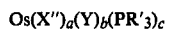

wherein X" is independently selected from hydrogen and halogen; Y is independently selected from NO, CO, NH₃ and N₂, and R' is a hydrocarbyl group independently selected from alkyl, aryl, aralkyl and alkaryl; "a" and "b" are numbers of from 0 to about 3, "c" is a number of 2 to 4; and the sum of a, b, and c is selected in conjunction with the valence of Os to achieve a neutral complex.

30. The process of claim 29 wherein the osmium complex is selected from the group consisting of OsH₂N₂(Pφ₃)₃; OsH₂(Pφ₃)₄; OsCl₂(CO)(Pφ₃)₃; OsCl(CO)(NO)(Pφ₃)₂; OsCl₂(Pφ₃)₃; OsCl₃(NO)(Pφ₃)₂; OsCl(NO)(Pφ₃)₂; OsHCl(CO)(PEt₂φ)₃; OsCl₂(NH₃)(PEt₂φ)₃.

31. The process of claim 27 wherein the osmium complex is selected from the group consisting of [Os(2,2'-bipyridine)₃]⁺² and [Os(NH₃)₅X]⁺² wherein X is halide.

32. The process of claim 27 wherein the osmium complex is selected from the group consisting of [OsO₃N]⁻, K[OsO₃N]; and OsO₃NC(CH₃)₃.

33. The process of any one of claims 1 to 32 wherein the support onto which the osmium compound is adsorbed is selected from the group consisting of alkaline earth metal oxides, an oxide of the lanthanide series of elements; alkaline earth metal orthosilicates, heteropolytungstates, heteropolymolybdates, Hg₂I₂, HgI₂, PbI₂, Al₂O₃.B₂O₃, SiO₂.B₂O₃, alumina, silica, silica gel, silica-alumina, silicon carbide, titania, titania-silica, carbon, a weak base ion exchange resin, a strong base ion exchange resin, a weak acid ion exchange resin, a strong acid ion exchange resin, and a crystalline aluminosilicate zeolite.

34. The process of any one of claims 1 to 32 wherein the support is magnesium oxide.

35. The process of claim 1 wherein the support is a strong basic ion-exchange resin at least partially exchanged with a halide counter ion.

36. The process of claim 35 wherein the halide ion is iodide.

37. The process of claim 33 wherein the osmium compound is chemically adsorbed on the support.

38. The process of claim 1 wherein a co-catalyst is employed and is selected from at least one member of the group consisting of:
(1) alkali or alkaline earth metal halide;
(2) alkali or alkaline earth metal hydroxide or oxide;
(3) alkali or alkaline earth metal: carboxylate, aryloate, or aryolate;
(4) alkali or alkaline earth metal pseudo halide;
(5) tetra hydrocarbyl ammonium, or phosphonium: hydroxide, halide, pseudo halide, carboxylate, aryloate, or aryolate;
(6) transition metal: halide, porphyrin, pseudo halide, carboxylate, or aryolate said transition metal being selected from the group consisting of Fe, Co, Ni, Cu, V, Cr, Mn, Sc, Ti, Mo, Ru, Rh, Pd, and W;
(7) hydrogen halide;
(8) halogenated hydrocarbons wherein the hydrocarbyl portion thereof is selected from the group consisting of saturated aliphatic, saturated alicyclic and aromatic;
(9) Group III-b, IV-b, V-b, and VI-b metal halide, said metal being selected from the group consisting of Al, Ga, In, Tl, Ge, Sn, Pb, P, As, Sb, Bi, S, Se, Te, and Po;
(10) halogen; and
(11) mixtures of any member of any of said groups with any other member of any of said groups.

39. The process of claim 1 wherein the co-catalyst comprises at least one member selected from the group consisting of alkali metal hydroxide, alkaline earth metal hydroxide, alkali metal oxide, alkaline earth metal oxide, alkali metal halide, alkaline earth metal halide, alkali metal acetate, alkaline earth metal acetate, tetra alkyl ammonium halide wherein the alkyl group contains from about 1 to about 3 carbons, tetra alkyl phosphonium halide wherein the alkyl group contains from about 1 to about 3 carbons; and halogenated hydrocarbons wherein the hydrocarbyl portion thereof is selected from the group consisting of alkyl, aryl, aralkyl, alkaryl, and cycloalkyl.

40. The process of claim 39 wherein the co-catalyst comprises at least one member selected from the group consisting of alkali metal halide, alkaline earth metal halide, and halogenated hydrocarbon.

41. The process of claim 1 wherein the co-catalyst and support is magnesium oxide.

42. The process of claim 38 wherein the oxidant is oxygen and the co-catalyst comprises at least one member of said Group (6) transition metal containing co-catalyst.

43. The process of claim 1 wherein the oxidant comprises at least one organic hydroperoxide.

44. The process of claim 43 wherein the oxidant is selected from the group consisting of t-butyl hydroperoxide, ethyl benzyl hydroperoxide, t-amyl hydroperoxide, and 2-butyl hydroperoxide.

45. The process of claim 1 wherein the oxidant is H₂O₂ and the pH of the liquid admixture is from neutral to basic.

46. The process of claim 1 wherein said admixture additionally comprises an inert solvent in which the supported osmium catalyst is insoluble.

47. A process for hydroxylating olefins which comprises:
1. providing a liquid reaction mixture comprising:
   (a) at least one olefin having at least one ethylenic unsaturation;
   (b) at least one organic hydroperoxide;
   (c) water; and
   (d) at least one co-catalyst selected from the group consisting of alkali metal halide, alkaline earth metal halide; tetra alkyl ammonium halide, tetra alkyl phosphonium halide, transition metal halide said transition metal being selected from the group consisting of Cu, Fe, Ni, Co, and Mn, and halogenated hydrocarbon said hydrocarbyl portion thereof being selected from saturated aliphatic, saturated alicyclic, and aromatic; and
2. contacting said liquid reaction mixture with a supported osmium catalyst in a manner and under conditions sufficient to convert at least one of said ethylenic unsaturation to its corresponding diol, said supported osmium catalyst comprising a support and an osmium compound adsorbed on said support wherein;
(i) said support is insoluble in said liquid reaction mixture under hydroxylation reaction conditions and is selected from the group consisting of magnesium oxide, alumina, carbon, silica, and a styrene-divinyl benzene based ion-exchange resin; and
(ii) said osmium containing compound is initially adsorbed on said support as a member selected from the group consisting of $Os_3(CO)_{12}$, $OsO_4$ and osmium metal.

48. The process of claim 47 wherein the co-catalyst comprises at least one member selected from the group consisting of alkali metal halide, alkaline earth metal halide, and halogenated hydrocarbon, and said supported osmium catalyst comprises $Os_3(CO)_{12}$ chemically adsorbed on a magnesium oxide support.

49. The process of claim 48 wherein said olefin is selected from the group consisting of ethylene and propylene.

50. The process of claim 47 wherein the supported osmium catalyst comprises said ion-exchange resin which has been exhausted with a halide ion and on which $OsO_4$ is chemically adsorbed.

51. The process of claim 47 which comprises the additional step of separating said liquid reaction mixture from said supported osmium catalyst; and recovering the hydroxylated product from the reaction mixture.

* * * * *